(12) United States Patent
Fliss

(10) Patent No.: US 6,495,538 B2
(45) Date of Patent: *Dec. 17, 2002

(54) ZINC IONOPHORES AS THERAPEUTIC AGENTS

(75) Inventor: Henry Fliss, Ottawa (CA)

(73) Assignee: Zinc Therapeutics, Canada Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/759,091

(22) Filed: Jan. 12, 2001

(65) Prior Publication Data

US 2001/0036939 A1 Nov. 1, 2001

Related U.S. Application Data

(63) Continuation-in-part of application No. 09/602,829, filed on Jun. 23, 2000.
(60) Provisional application No. 60/140,632, filed on Jun. 23, 1999.
(51) Int. Cl.[7] .................. A61K 31/555; A61K 31/355; A61K 31/27; A61K 31/07
(52) U.S. Cl. ................ 514/188; 514/458; 514/476; 514/725
(58) Field of Search ............................. 514/458, 725, 514/188, 476

(56) References Cited

FOREIGN PATENT DOCUMENTS

JP          10-101566          4/1998

OTHER PUBLICATIONS

Martindale, The Extra pharmacopeia, 28th ed, pp. 500–501. (1982).*
Treves, S. et al., "Apoptosis is dependent on intracellular zinc and independent of intracellular calcium in lymphocytes", *Experimental Cell Research*, 211(2): 339–343 (1994).
Zalewski, P. et al., "Correlation of apoptosis with change in intracellular labile Zn(II) using Zinquin (2–methyl–8–p–toluenesulphonamido–6–quino lyloxy)acetic acid), a new specific fluorescent probe for Zn(II)", *Biochemical Journal*, 296(2): 403–408 (1993).
Zalewski, P. et al., "Physiological Role For Zinc in Prevention of Apoptosis Gene–Directed Death", *Biochemistry International*, 24(6): 1093–1102 (1991).
Matsushita K. et al., "Effect of systemic zinc administration on delayed neuronal death in the gerbil hippocampus", *Brain Research*, 743(1–2): 362–365 (1996).
Carmody, R. et al., "Reactive oxygen species as mediators of photoreceptor apoptosis in vitro", *Experimental Cell Research*, 248(2): 520–530 (1999).
Tagami,.M. et al., "Vitamin E prevents apoptosis in hippocampal neurons caused by cerebral ischemia and reperfusion in stroke–prone spontaneously hypertensive rats", *Laboratory Investigation*, 79(5): 609–615 (1999).
Tagami, M. et al., "Vitamin E prevents apoptosis in cortical neurons during hypoxia and oxygen reperfusion", *Laboratory Investigation*, 78(11): 1415–1429 (1998).
Tagami, M. et al., "Vitamin E prevents apoptosis in hippocampal nerons caused by cerebral ischemia and reperfusion in stroke–prone spontaneously hypertensive rats", *Stroke*, 29(1): 279 (1998).
Kubota, M. et al., "Neuroprotective effect of zinc complex with high membrane permeability after transient cerebral ischemia in the rat", *Biology and Medicine*, 154–155 (1998) with English language abstract.

* cited by examiner

Primary Examiner—Raymond Henley, III
(74) Attorney, Agent, or Firm—Scully, Scott, Muryphy & Presser

(57) ABSTRACT

The present invention provides methods and compositions comprising one or more zinc ionophores for protecting tissue from the harmful effects of apoptosis in patients in need thereof. Concentrations of zinc-pyrithione and diethyldithiocarbamate in the picomolar to nanomolar range have a strong protective effect against apoptosis.

26 Claims, 24 Drawing Sheets

P-values vs. vehicle

Effects of Zinc Pyrithione on HSP-70 in heart n=8-9
*p<0.01 vs DMSO

Effects of Zinc Pyrithione on SP1 in Brain n=3-6
*p<0.01

Effects of zinc pyrithione on kainic acid induced damage in rat brain areas

Effects zinc pyrithione on the severity of kainic acid induced seizures in rats

PROTECTIVE EFFECTS OF ZINC PYRITHIONE IN PC12 CELLS

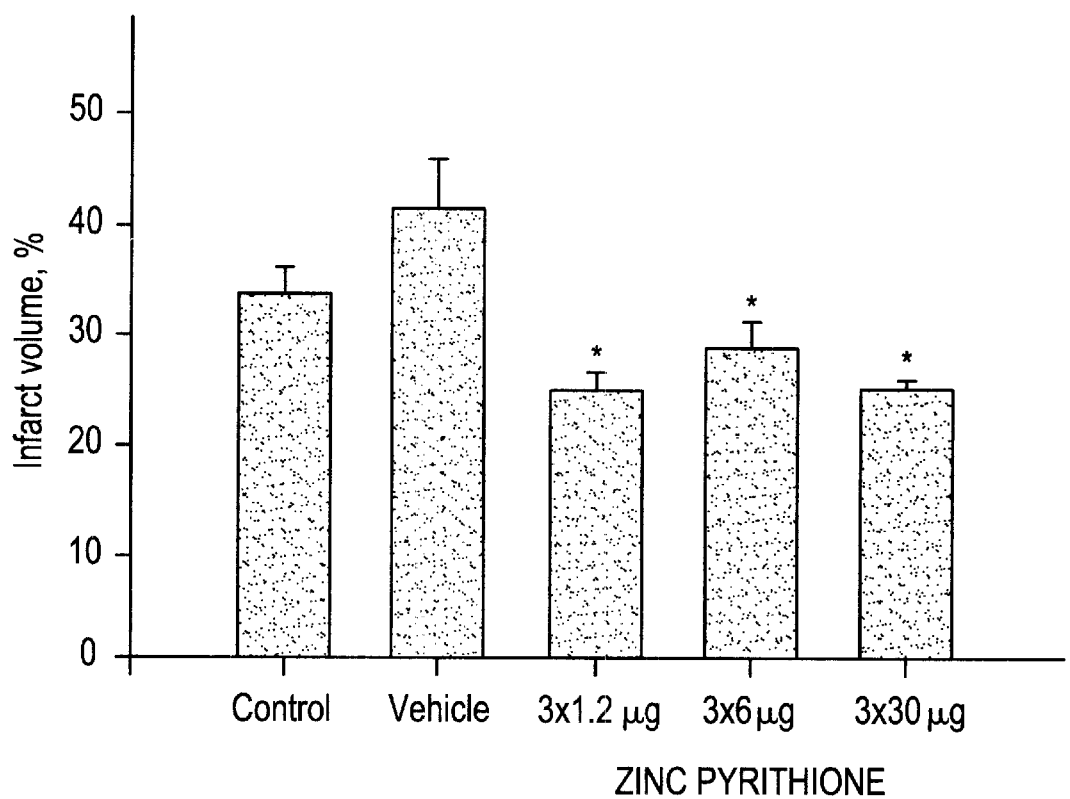

ZINC IONOPHORES AS THERAPEUTIC AGENTS

RELATED APPLICATIONS

This application is a continuation-in-part of U.S. Ser. No. 09/602,829, filed Jun. 23, 2000, which application claims the benefit of U.S. Provisional Application Ser. No. 60/140,632, filed Jun. 23, 1999.

FIELD OF THE INVENTION

The present invention relates to a method of protecting tissue from apoptosis using zinc ionophores. The present invention also relates to a method of protecting cells against the harmful effects of injurious agents, for example, oxidants, TNFα, neurotoxins, ischemia and radiation.

BACKGROUND OF THE INVENTION

Zinc plays a critical role in cellular biology, and is involved in virtually every important cellular process such as transcription, translation, ion transport, and others (O'Halloran, T. V. (1993) *Science* 261:715–725; Cousins, R. J. (1994) *Annu.Rev.Nutr.* 14:449–469; Harrison, N. L. et al. (1994) *Neuropharmacology* 33:935–952; Berg, J. M. et al. (1996) *Science* 271:1081–1085). The involvement of cellular zinc in apoptosis has been recognized for close to 20 years (Sunderman, F. W.,Jr. (1995) *Ann.Clin.Lab.Sci.* 25:134–142; Fraker, P. J. et al. (1997) *Proc.Soc.Exp.Biol.Med.* 215:229–236.). However, the full nature of this involvement is not fully understood. Apoptosis is a form of programmed cell death normally activated under physiological conditions, such as involution in tissue remodelling during morphogenesis, and several immunological processes. The apoptotic process is characterized by cell shrinkage, chromatin condensation, and internucleosomal degradation of the cell's DNA (Verhaegen et al. (1995) *Biochem. Pharmacol.* 50(7):1021–1029).

Numerous in vitro studies have been done recently in an attempt to elucidate the role of intracellular zinc. Although some studies have suggested that zinc may actually induce apoptosis (Xu, J. et al. (1996) *Am.J.Physiol.* 270:G60–G70; Kim, Y. H. et al., (1999) *Neuroscience* 89:175–182), most have concluded that increasing the intracellular concentrations of zinc blocks apoptosis (Sunderman, F. W.,Jr. (1995) *Ann.Clin.Lab.Sci.* 25:134–142; Adebodun, F. et al. (1995) *J.Cell.Physiol.* 163:80–86; Zalewski, P. D., et al. (1993) *Biochem.J.* 296:403–408), and that decreasing the zinc concentration promotes apoptosis (Jiang, S., et al. (1995) *Lab.Invest.* 73:111–117; Treves, S., et al. (1994) *Exp.Cell Res.* 211:339–343; Ahn, Y. H., et al. (1998) Exp.Neurol. 154:47–56). The manner in which increased intracellular zinc affords protection against apoptosis is not clear. (Truong-Tran, A. Q. et al., (2000) J. Nutr. 130:1459S–1466S) One theory proposes that zinc inactivates the intracellular endonuclease(s) responsible for apoptotic DNA fragmentation (Shiokawa, D., et al. (1994) *Eur.J.Biochem.* 226:23–30; Yao, M. et al., (1996) *J.Mol..Cell.Cardiol.* 28:95–101). Other recent studies have suggested that zinc can inhibit caspases (Jiang, S., et al. (1997) *Cell Death Differ.* 4:39–50; Perry, D. K., et al. (1997) *J.Biol.Chem.* 272:18530–18533; Maret, W., et al. (1999) *Proc.Natl.Acad.Sci.USA* 96:1936–1940), or block the activation of caspases (Aiuchi, T., et al. (1998) *J.Biochem.* 124:300–303). However, in view of the large number of intracellular roles played by zinc, it seems likely that its anti-apoptotic mechanisms may be more complex, possibly involving gene expression and cellular signalling pathways. In fact, recent studies support a role for zinc transients in intracellular signalling and gene expression (O'Halloran, T. V. (1993) *Science* 261:715–725; Berg, J. M., et al., (1996) *Science* 271:1081–1085).

In contrast to the large number of in vitro studies, very few studies have attempted to examine the protective effects of zinc in vivo. It is important to note that most of the studies that have explored this possibility have focused on the pretreatment of tissues with zinc prior to injury. Using this approach, a number of studies have demonstrated that pretreatment of animals with zinc at least 24 hours prior to injury provided some measure of protection against apoptosis (Thomas, D. J. et al., (1991) *Toxicology* 68:327–337; Matsushita, K., et al., (1996) *Brain Res.* 743:362–365; Klosterhalfen, B., et al., (1997) *Shock* 7:254–262), presumably as a result of the well established ability of zinc to boost the immune system (Cunningham-Rundles, S., et al., (1990) *Ann.N.Y.Acad.Sci.* 587:113–122). Also, one study showed that several days of zinc dietary supplementation concomitant with i.p. injection of carbon tetrachloride protected against liver apoptosis (Cabre, M. et al. (1999) *J. Hepatol.* 31:228–234). However, no studies have demonstrated the efficacy of zinc when administered acutely and post-injury, a much more clinically relevant setting.

Zinc-pyrithione (zinc pyridinethione, $C_{10}H_8N_2O_2S_2Zn$, MW 317.75, commercially available from Sigma) is the active ingredient in the anti-dandruff shampoo Head & Shoulders® (U.S. Pat. Nos. 3,236,733, and 3,281,366, both 1966), as well as a number of other topical skin treatment formulations. It is a fungicide and bactericide at high concentrations. It is highly lipophilic and therefore penetrates membranes easily. This permits zinc pyrithione to transport zinc across cell membranes, thereby conferring on this compound (i.e. zinc pyrithione) the properties of a zinc ionophore. The anti-apoptotic effect of zinc pyrithione was first observed in vitro by Zalewski and coworkers, who showed that micromolar concentrations of this compound protected lymphocytic leukemia cells against colchicine-induced apoptosis (Giannakis, C., et al. (1991) *Biochem. Biophys. Res. Commun.* 181:915–920). The rationale for the use of this zinc ionophore was to facilitate the transport of $Zn^{2+}$ into the target cells. This is necessitated by the fact that all eukaryotic cells strictly regulate the membrane transport of $Zn^{2+}$, making it very difficult to modulate the intracellular concentration and distribution of $Zn^{2+}$. Zalewski's group has since published a number of other studies, all of them in vitro, confirming the ability of micromolar concentrations of zinc-pyrithione to rapidly transport $Zn^{2+}$ into cells and to thereby prevent apoptosis (Zalewski, P. D., et al. (1994) supra; Zalewski, P. D., et al. (1993) *Biochem.J.* 296:403–408). One confirmatory study, also in vitro, has been published from another laboratory (Tempel, K. -H. et al., (1993) *Arch.Toxicol.* 67:318–324).

In addition to zinc-pyrithione, another group of zinc ionophores, the dithiocarbamates, has been shown to affect apoptosis in vitro. (Orrenius, S. et al. (1996) *Biochem. Soc. Trans.* 24:1032–1038; Stefan, C. et al. (1997) *Chem. Res. Toxicol.* 10:636–643; Erl, W. et al., (2000) *Am. J. Physiol.* 278:C1116–C1125). However, no attempts have been made to examine in vivo the protective effects of zinc-pyrithione, zinc-bound dithiocarbamates or any other known zinc ionophore at nanomolar or picomolar concentrations.

SUMMARY OF THE INVENTION

The ability of zinc-pyrithione and zinc-diethyldithiocarbamates to protect tissue against apoptosis in three models of in vivo injury, as well as two in vitro models is presented. In each case a pronounced anti-apoptotic effect was achieved. The ability of zinc-pyrithione, zinc diethyldithiocarbamates and zinc 5,7-diodo-8-hydroxyquinoline to treat and prevent seizures is also provided.

Thus, according to the present invention there is provided a method to protect against apoptosis and treat seizures using one or more zinc ionophores.

In one embodiment of the present invention there is provided a method of treating apoptosis in mammalian tissue such as heart, brain, and eye tissue by administering to a mammalian subject in need thereof a pharmaceutically effective amount of at least one zinc ionophore.

In another embodiment of the present invention there is provided a pharmaceutical composition comprising a zinc ionophore and a pharmaceutically acceptable carrier.

In a further embodiment of the present invention there is provided a method of protecting against the harmful effects of injurious agents such as TNFα, neurotoxins, ischemia and radiation by administering to a subject in need of such protection an effective amount of a zinc ionophore.

In a still further embodiment of the present invention there is provided a method of treating or preventing seizures by administering to a subject in need thereof a pharmaceutically effective amount of at least one zinc ionophore.

BRIEF DESCRIPTION OF THE FIGURES

These and other features of the invention will become more apparent from the following description in which reference is made to the appended drawings wherein:

FIG. 21A shows the administration of zinc-pyrithione decreased infarct volumes in mouse brain.

DETAILED DESCRIPTION OF THE INVENTION

Figure 1:
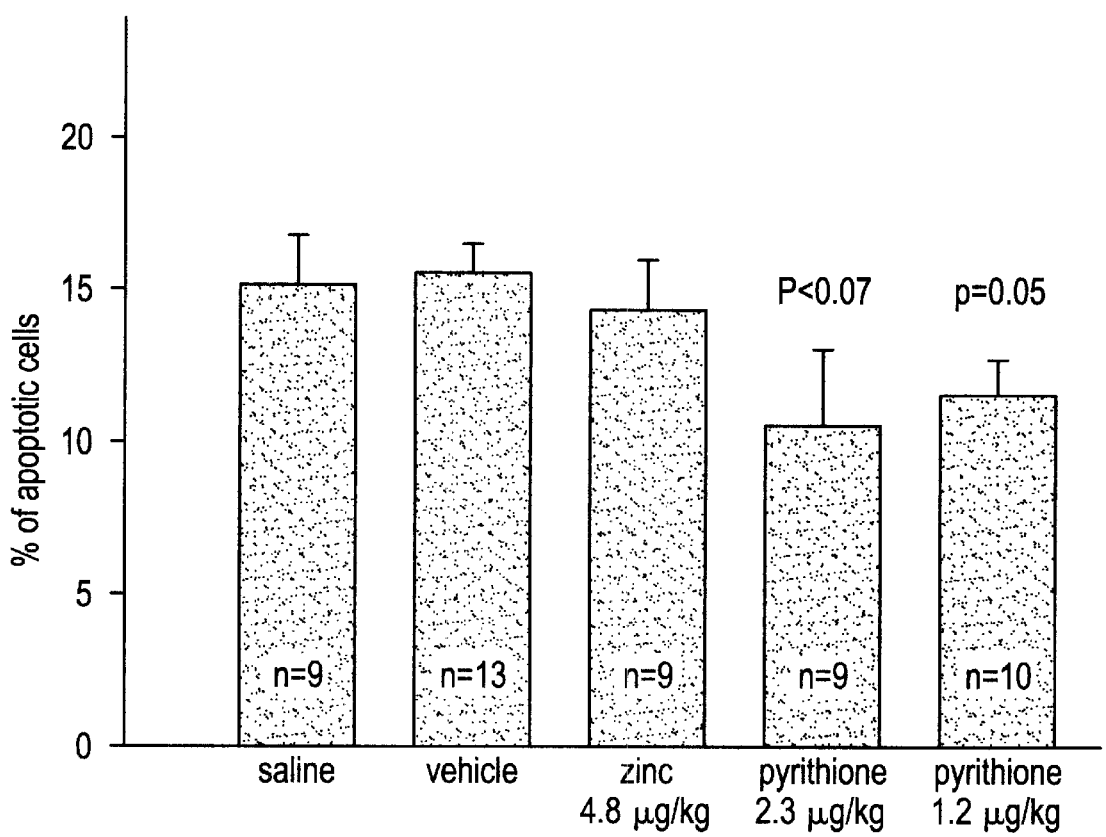
FIG. 1 shows the effect of zinc pyrithione on rat cardiac apoptosis.

The present invention is directed to a method of protecting tissue from the harmful effects of apoptosis and treating seizures by administering an effective amount of one or more zinc ionophores to a subject in need thereof. By "zinc ionophore" is meant a therapeutic compound complexed with zinc ions that is capable of carrying zinc ions across cell membranes. In accordance with the present invention "treating" includes preventing, blocking, inhibiting, attenuating, protecting against and reducing the occurrence of e.g., the harmful effects of apoptosis and seizures.

Previous studies have shown in vitro that treatment of injured cells with zinc can block apoptosis. In these studies the effectiveness of a zinc ionophore was demonstrated using high concentrations, ranging from 3 $\mu$M to 5 mM. It was found, according to the present invention that such concentrations are not suitable for use in any in vivo method. Thus, according to the present invention, small concentrations of a zinc ionophore in the nanomolar and picomolar range, such as from about 10 pM to about 1 $\mu$M, protect tissue from the harmful effects of apoptosis.

Thus, according to the present invention the concentration of zinc ionophore used to protect tissue from the harmful effects of apoptosis ranges from about 0.005 $\mu$g zinc ionophore per kg of body weight to about 5 mg zinc ionophore per kg of body weight (i.e. about 600 pM zinc ionophore to about 15 $\mu$M zinc ionophore). In a further embodiment of the present invention the concentration of zinc ionophore used to protect tissue from the harmful effects of apoptosis ranges from about 1.0 $\mu$g zinc ionophore per kg of body weight to about 800 $\mu$g zinc ionophore per kg of body weight. Preferably the concentration of zinc ionophore used to protect tissue from the harmful effects of apoptosis ranges from about 0.2 $\mu$g zinc ionophore per kg of body weight to about 600 $\mu$g zinc ionophore per kg of body weight.

In a further embodiment of the present invention the concentration of zinc ionophore used to protect tissue from the harmful effects of apoptosis is about 0.9 mg/kg body weight, or about 0.18 mg zinc/kg body weight.

According to the present invention, any compound capable of binding zinc with moderate affinity and having sufficient lipophilic properties to penetrate cell membranes is capable of effecting the protection demonstrated in the present invention with e.g., zinc-pyrithione. The following are examples of compounds which have been shown in accordance with the present invention to possess zinc-ionophore properties: zinc pyrithione, the heterocyclic amines including, for example, 5,7-Diiodo-8-hydroxyquinoline, and 8-Hydroxyquinoline; the dithiocarbamates including, for example, pyrrolidine dithiocarbamate and diethyldithiocarbamate, disulfiram and dimethyldithiocarbamate; and Vitamins including, but not limited to, Vitamin E and Vitamin A. Properties associated with zinc ionophores include, but are not limited to, an ability to alter cytosolic PKC-α content and an ability to alter the nuclear activity of transcription factors NF-kB, AP-1 and Sp1. According to the present invention zinc-pyrithione was shown to operate at the cell signalling level, as demonstrated by its ability to alter cytosolic PKC-α content. Further, according to the present invention, zinc-pyrithione was shown to operate at the transcriptional level, as demonstrated by its ability to alter the nuclear activity of transcription factors NF-kB, AP-1 and Sp1. Still further, according to the present invention zinc-pyrithione was shown to upregulate cytoprotective proteins, for example HSP70.

In accordance with the present invention the zinc ionophores protect against neuronal cell loss in stroke patients. For example, zinc pyrithione demonstrates neuroprotective properties, showing protection against cell loss in the selectively vulnerable zone of the CA1 region of the hippocampus in a rat model of severe global ischemia. In the mouse model of severe focal ischemia, zinc pyrithione demonstrates neuroprotective properties, significantly decreasing brain infarct volume and neurological deficit.

The zinc ionophores of the present invention are versatile in their efficacy and can be used to treat diseases associated with the human eye including hereditary degenerative retinopathies, including macular degeneration and retinitis pigmentosa, for example. Other diseases of the eye treatable with the zinc ionophores of the present invention include, but are not limited to cataracts (diabetic and chemically induced, for example), glaucoma, inflammatory eye diseases, corneal apoptosis associated with transplantation and Fuchs' dystrophy.

The zinc ionophores of the present invention can also be used to treat neurodegenerative diseases such as Alzheimer's Disease, Parkinson's Disease, Huntington's Disease, Amyotrophic lateral sclerosis (ALS) and multiple sclerosis, for example.

The zinc ionophores of the present invention also exhibit anti-epileptic efficacy. In accordance with the present invention "anti-epileptic" means "anti-convulsive" and "anti-seizure". For example, zinc diethyldithiocarbamate demonstrates an anti-seizure effect in a mouse model of seizure. Using the total elimination of tonic extension as the principal criterion for anti-seizure efficacy, zinc diethyldithiocarbamate showed statistically significant ability to block tonic seizures. Accordingly, the present invention provides a method for attenuating both the duration and severity of seizures in mammalian subjects, including humans.

In use, at least one zinc ionophore, according to the present invention is administered in a pharmaceutically effective amount to a subject in need thereof in a pharmaceutical carrier by intravenous, intramuscular, subcutaneous, or intracerebroventricular injection or by oral administration or topical application. In accordance with the present invention, one zinc ionophore may be administered, preferably by the intravenous injection route, alone or in conjunction with a second, different zinc ionophore. By "in conjunction with" is meant together, substantially simultaneously or sequentially. In one embodiment, the zinc ionophores of the present invention, are administered acutely, such as, for example, substantially immediately following an injury that results in apoptosis, such as a stroke. The zinc ionophores may therefore be administered for a short course of treatment, such as for about 1 day to about 1 week. In another embodiment, the zinc ionophores of the present invention may be administered over a longer period of time to ameliorate chronic apoptotic episodes, such as, for example, for about one week to several months depending upon the condition to be treated.

By "pharmaceutically effective amount" as used herein is meant an amount of zinc ionophore, e.g., zinc-pyrithione, high enough to significantly positively modify the condition to be treated but low enough to avoid serious side effects (at a reasonable benefit/risk ratio), within the scope of sound medical judgment. A pharmaceutically effective amount of zinc ionophore will vary with the particular goal to be achieved, the age and physical condition of the patient being treated, the severity of the underlying disease, the duration of treatment, the nature of concurrent therapy and the specific zinc ionophore employed. For example, a therapeutically effective amount of a zinc ionophore administered to a child or a neonate will be reduced proportionately in accordance with sound medical judgment. The effective amount of zinc ionophore will thus be the minimum amount which will provide the desired anti-apoptotic effect.

A decided practical advantage of the present invention is that the zinc ionophore, e.g. zinc-pyrithione, may be administered in a convenient manner such as by the, intravenous, intramuscular, subcutaneous, oral or intracerebroventricular injection routes or by topical application, such as in eye drops or eye mist compositions. Depending on the route of administration, the active ingredients which comprise zinc ionophores may be required to be coated in a material to protect the zinc ionophores from the action of enzymes, acids and other natural conditions which may inactivate the zinc ionophores. In order to administer zinc ionophores by other than parenteral administration, the ionophores should be coated by, or administered with, a material to prevent inactivation. For example, the zinc ionophores of the present invention may be co-administered with enzyme inhibitors or in liposomes. Enzyme inhibitors include pancreatic trypsin inhibitor, and trasylol. Liposomes include water-in-oil-in-water P40 emulsions as well as conventional and specifically designed liposomes.

The zinc ionophores may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the zinc ionophore in the required amount in the appropriate solvent with various of the other ingredients enumerated above, as required, followed by filtered sterilization. Generally, dispersions are prepared by incorporating the various sterilized zinc ionophores into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient plus any additional desired ingredient from previously sterile-filtered solution thereof.

For oral therapeutic administration, the zinc ionophores may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains a zinc ionophore concentration sufficient to treat or block apoptosis in a patient.

The tablets, troches, pills, capsules, and the like, may contain the following: a binder such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, lactose or saccharin may be added or a flavoring agent such as peppermint, oil or wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules or zinc ionophore in suspension may be coated with shellac, sugar or both.

A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the zinc ionophore may be incorporated into sustained-release preparations and formulations.

By "pharmaceutically-acceptable carrier" as used herein is meant one or more compatible solid or liquid filler diluents or encapsulating substances. By "compatible" as used herein is meant that the components of the composition are capable of being comingled without interacting in a manner which would substantially decrease the pharmaceutical efficacy of the total composition under ordinary use situations.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present.

Accordingly, in a preferred form of protecting tissue from the harmful effects of apoptosis and seizures the subject is administered a therapeutically effective amount of at least one zinc ionophore and a pharmaceutically acceptable carrier in accordance with the present invention. The zinc ionophores of the present invention are also effective in treating ischemia. By "ischemia" is meant reduced blood flow that results in hypoxia in one or more organs including brain, heart, muscle and nervous tissue. For example, ischemia in the brain causes strokes; ischemia in the heart causes myocardial infarctions. Therefore, in a preferred form of treating ischemia the subject is administered a therapeutically effective amount of at least one zinc ionophore and a pharmaceutically acceptable carrier. A preferred subject is a human. A preferred zinc ionophore is zinc pyrithione. Another preferred zinc ionophore is zinc diethyldithiocarbamate.

The zinc ionophores of the present invention are effective against a wide range of injurious agents, for example, but not limited to: oxidants, TNFα, neurotoxins, or radiation.

Also defined within the present invention are compositions suitable for protecting tissue from the harmful effects of apoptosis which comprise one or more zinc ionophores and a pharmaceutically acceptable carrier.

Various modifications may be made without departing from the invention. The disclosure is to be construed as exemplary, rather than limiting, and such changes within the principles of the invention as are obvious to one skilled in the art are intended to be included within the scope of the claims.

The present invention will now be demonstrated using specific examples that are not to be construed as limiting.

EXAMPLE 1

Screening for Ionophores:

Cell Cultures:

Human umbilical vein endothelial cells (HUVEC) were purchased from Clonetics (San Diego, Calif.) and passages 2–4 were used for these studies. Cells were cultured on flame-sterilized glass coverslips in Endothelial Basal Medium (Clonetics) supplemented with 10 ng/ml human recombinant epidermal growth factor, 1.0 ug/ml hydrocortisone, 50 ug/ml gentamicin, 50 ng/ml amphotetericin B, 12 ug/ml bovine brain extract and 2% v/v fetal bovine serum (all from Clonetics), in a humidified chamber at 37° C. and 5% $CO_2$. To maintain cell populations, proliferating HUVEC were passaged at 80–90% confluency.

Cardiac myocytes were isolated from the ventricular septum of adult rabbit hearts, following collagenase digestion, in a manner similar to that described previously (Turan, B. et al., (1997) *Am. J. Physiol.* 272:H2095–H2106). The modification consisted of introducing low concentrations of $CaCl_2$ during the perfusion with collagenase and the dispersion of the myocytes. Hearts were perfused for about 2 min by gravity under a hydrostatic pressure of 1 m, with a nominally $Ca^{2+}$-free solution containing (in mM): NaCl, 145; KCl, 5; $MgSO_4$, 1.2; $Na_2HPO_4$, 1.8; HEPES, 5; glucose, 10; pH adjusted to 7.4 with NaOH. Forty ml of this perfusate were then supplemented with collagenase (1 mg/ml) and perfusion was continued with recirculation. Within 2–3 min, this treatment resulted in a complete loss of ventricular pressure. The flow rate was then adjusted to 15 ml/min and 50 μM CaCl$_2$ was added to the collagenase solution. Perfusion with this solution was continued for another 15 to 18 min, followed by a 2 min washout of the enzyme with fresh perfusate containing 100 μM CaCl$_2$ and no collagenase. The hearts were then removed from the apparatus and the ventricular septum isolated and minced. Dissociation of the cells was obtained by gentle agitation of the minced tissue in 50 ml of the same perfusing solution. Following filtration through a 200 μm nylon mesh, the cells were allowed to settle and the supernatant was replaced with a solution containing 2 mM CaCl$_2$. Cells were kept at 37° C. in this pre-oxygenated solution and were studied within 8 hours after isolation, cellular viability was ensured by regularly replacing the incubation solution.

Primary cultures of mouse cerebellar granule neurons were obtained from dissociated cerebella of postnatal day 8 or 9 mice according to the following protocol (Cregan et al., (1999) *J. Neurosci.* 19:7860–7869, incorporated herein by reference). Brains were removed and placed into separate dishes containing solution A (124 mM NaCl, 5.37 mM KCl, 1 mM NaH2 PO4, 1.2 mM MgSO4, 14.5 mM D-(1)-glucose, 25 mM HEPES, 3 mg/ml BSA, pH 7.4) in which the cerebella were dissected, meninges removed, and tissue sliced into small pieces. The tissue was briefly centrifuged and transferred to solution A containing 0.25 mg/ml trypsin, then incubated at 37° C. for 18 min. After the addition of 0.082 mg/ml trypsin inhibitor (Boehringer Mannheim, Indianapolis, IN) and 0.25 mg/ml DNase I (Boehringer Mannheim), the tissue was incubated at 25° C. for 2 min. After a brief centrifugation, the resulting pellet was gently titrated in solution A yielding suspension that was further incubated for 10 min at 25° C. in solution A containing 2.7 mM MgSO4 and 0.03 mM CaCl2. After a final centrifugation the pellet was resuspended in EMEM media (Sigma, St. Louis, Mo.) containing 10% dialyzed FBS (Sigma), 25 mM KCl, 2 mM glutamine (Life Technologies BRL, Gaithersburg, Md.), 25 mM glucose, and 0.1 mg/ml gentamycin (Sigma) and filtered through a cell strainer (size 70 μm; Falcon). Cells were plated on glass coverslips coated with poly-D-lysine (Sigma) in Nunc four-well dishes at a density of 1.5×10$^6$ cells per milliliter of medium. Cytosine-β-arabinoside (10 μM; Sigma) was added 24 hr after plating.

Test Compounds:

Several test compounds with potential zinc-ionophore activity were screened for their ability to transport zinc into selected target cells. In order to ascertain that the transported ion was indeed Zn$^{2+}$, and not some other divalent cation contaminant, the test compounds were first complexed with zinc. In addition to the zinc-complexed ionophores (holo-ionophores), the zinc-free forms of these compounds (apo-ionophores) were also tested for the purpose of comparison. Whenever possible, purified holo-ionophores were purchased commercially (e.g. zinc-diethyldithiocarbamate, Sigma-Aldrich). However, in most cases only the apo-ionophores were available commercially. The holo-ionophores were therefore prepared in our laboratory. Since zinc ionophores (e.g. pyrithione, diethyldithiocarbamate, 8-hydroxyquinoline) complex with zinc in a 2:1 molar ratio (ionophore:zinc), stock solutions (generally 15.7 mM) of holo-ionophores were prepared by combining the apo-ionophore with ZnCl$_2$ in a 2:1 molar ratio either in water or DMSO, depending on the solubility of the reactants, and incubating at room temperature for 15 min. The holo-ionophores were then stored at −20° C. Immediately prior to screening, the stock solutions of these test compounds were thawed and diluted in the superfusion buffer to give a final concentration of 1 μM of the holo-ionophore. When testing the apo-ionophores, an equivalent molar concentration of the ionophore in the superfusion buffer (2 μM) was used.

Ionophore Screening:

Screening of the test compounds was performed with cultured HUVEC, isolated cardiac myocytes, and cultured cerebellar neurons following an approach described previously (Turan et al., (1997) *Am. J. Physiol.* 272:H2095–H2106). Immediately prior to screening, the cells were loaded with Fura-2, a zinc and calcium-sensitive indicator, by incubating the cells for 30 min in medium containing 4 μM Fura-2-am (Molecular Probes). Glass coverslips bearing HUVEC or cerebellar cells were placed directly in a superfusion chamber on the stage of an epifluorescence inverted microscope (Nikon Diaphot-DM). With isolated myocytes, an aliquot of Fura-2 loaded cell suspension was placed in the superfusion chamber and the cells were allowed to adhere to the glass bottom of the chamber before superfusion was started. The microscope field of view was adjusted to include one or more individual cells. To establish baseline fluorescence, the cells were first superfused for a few minutes with a superfusing solution containing the following (in mM): NaCl, 140; KCl, 5; MgCl$_2$, 1; CaCl$_2$, 2, HEPES, 5; glucose, 10; pH adjusted to 7.4 with NaOH. The flow rate was maintained at approximately 3 ml/min and the temperature at 37° C. The cells were then superfused with superfusion buffer containing a test compound and the fluorescence at 505 nm was recorded in response to excitation at 340 nm and 380 nm. The slope of the fluorescence intensity ratio in response to excitation at 340 and 380 nm was used to determine ionophore activity. In each test, the membrane-permeant heavy metal chelator N,N,N',N',-tetrakis(2-pyridylmethyl)ethylenediamine (TPEN, 30 μM) was added to the superfusate at the end of the run. Since TPEN does not chelate Ca$^{2+}$, loss of fluorescence in response to TPEN addition confirmed that the fluorescence was attributable to zinc. In cases where test holo-ionophores did not demonstrate zinc-ionophore activity, the validity of the negative observations was confirmed by adding zinc-pyrithione (1 μM) to the superfusing solution at the end of the test. An increase in fluorescence in response to the added zinc-pyrithione confirmed that the cell being tested was viable and responsive.

Approximately 50 test compounds were screened for ionophore activity using this approach (See Table 1). Of those, three groups of compounds were found to be particularly active zinc ionophores: pyrithione, dithiocarbamates, and hydroxyquinolines. Several compounds which do not belong to these groups also showed ionophore activity but at a lower level. The ionophore activity of pyrithione appeared to be comparable in all three cell types tested, as were the activities of diethyldithiocarbamate and 5,7-diiodo-8-hydroxyquinoline.

TABLE 1

EXAMPLE OF ZINC IONOPHORES
✓✓✓ - excellent
✓✓ - very good
✓ - good
ZINC-PYRITHIONE ✓✓✓
ZINC-DITHIOCARBAMATES
Pyrrolidinedithiocarbamate ✓✓
diethyldithiocarbamate ✓✓
Disulfiram ✓✓
dimethyldithiocarbamate ✓✓
ZINC-HETEROCYCLIC AMINES TABLE 1-continued 8-Hydroxyquinoline, ✓
5,7-Diiodo-8-hydroxyaquinoline ✓✓
ZINC-NSAID
Indomethacin ✓
ZINC-VITAMINS
Vitamin A (all-trans-retinol) ✓
Vitamin E (alpha-tocopherol) ✓

EXAMPLE 2
In Vivo Heart Model—Ischemic Injury.
Experimental Model:

This model was designed to simulate myocardial infarcts in rats. The protocol is a modification of one described in detail previously (Fliss, H. et al., (1996) Circ.Res. 79:949–956, incorporated herein by reference). Male Sprague-Dawley rats (250–350 g) were anesthetized, the chest was opened, a ligature was passed under the coronary artery and was then fashioned into a snare. The coronary artery was then occluded for a period of 45 minutes by tightening the snare, at which point the snare was released and the ischemic myocardium was reperfused. Following four hours of reperfusion the snare was re-tightened and the area-at-risk was delineated by intraveneous injection of the dye Evans blue. The rats were then killed immediately and the area-at-risk was collected for analysis.

Previous studies have demonstrated that this model produces extensive myocardial apoptosis (Fliss, H. (1996), supra). To examine the protective ability of zinc-pyrithione in this model, different cumulative doses (from 0.9 mg/kg body weight to 1.2 ug/kg body weight) of this reagent in a 4% DMSO solution in sterile saline were injected intravenously through a tail vein in three equal boluses: at the initiation of reperfusion, and at 1 and 2 h after the initiation of reperfusion. The total volume injected per rat was 1.5 ml. To examine the protective properties of zinc-diethyldithiocarbamate (ZnDDC) in this model, one dose of ZnDDC (0.21 ug/kg body weight) was tested in a manner identical to that used for zinc pyrithione.

Results:

The data collected to-date show a strong trend ($P<0.1$) towards anti-apoptotic effects with very low concentrations of zinc-pyrithione. TUNEL staining (Fliss, H. (1996), supra), as described below, was used to identify the percent of apoptotic myocytes in the affected tissue. Paraffin sections were deparaffinized and were subsequently permeabilized with methanol/acetone (1:1) for 10 min at RT, and were washed twice with PBS. They were then incubated with 20 $\mu$g/ml proteinase K in 25 mmol/L Tris-HCl (1 ml/section), pH 6.6, for 15 min at RT, were washed twice (15 min each) with water, were stained with Hoechst 33258 (0.05 mg/ml) for 30 min at RT, protected from light, and were washed 3 times (1 min each) with PBS. The sections were then incubated in 75 ml of a buffer solution containing 200 mmol/L potassium cacodylate, 2 mmol/L $CoCl_2$, 0.25 mg/ml bovine serum albumin, 25 mmol/L Tris-HCl, pH 6.6, 10 mmol/L biotin-16-dUTP (Boehringer Mannheim Canada, Laval, Quebec), and 25 units of terminal transferase (Boehringer), for 1 h at 37° C. in a humidified chamber. The reaction was terminated by washing the sections 3 times (1 min each) with PBS at RT.

The sections were then incubated with 1 ml of a staining solution containing 2.5 mg/ml fluorescein isothiocyanate-avidin (avidin-FITC), 4x saline-sodium citrate buffer, 0.1% Triton X-100, and 5% powdered milk, for 30 min at RT, protected from light. The sections were washed 3 times with PBS, were coverslipped in "anti-fade" solution containing 1 mg/ml p-phenylenediamine, 90% glycerol, in PBS, and histofluorescence was monitored with a Zeiss Axiophot microscope. Positive control samples were prepared by incubating sections with 10 units/ml DNAse I for 20 min at 37° C. prior to treatment with terminal transferase. The data demonstrate strong inhibition of apoptosis with 2.3 ug zinc-pyrithione per kg body weight when compared to DMSO carrier alone ($P=0.067$) (FIG. 1). Similar strong protection against apoptosis was observed with 1.2 ug/kg zinc-pyrithione ($P=0.053$). Since the zinc constitutes 20% by weight of zinc-pyrithione, the data suggest that about 0.20 to about 0.50 ug of zinc per kg body weight provides strong apoptosis protection. Strong protection ($P<0.05$) against apoptosis was also observed with the single dose of ZnDDC tested, i.e. 0.21 ug/kg body weight. Thus, the percent apoptotic nuclei in the ZnDDC treated hearts was $9.1\pm3.0$, in comparison to the vehicle only group in which the percent apoptosis was $15.6\pm1.2$.

Figure 2:
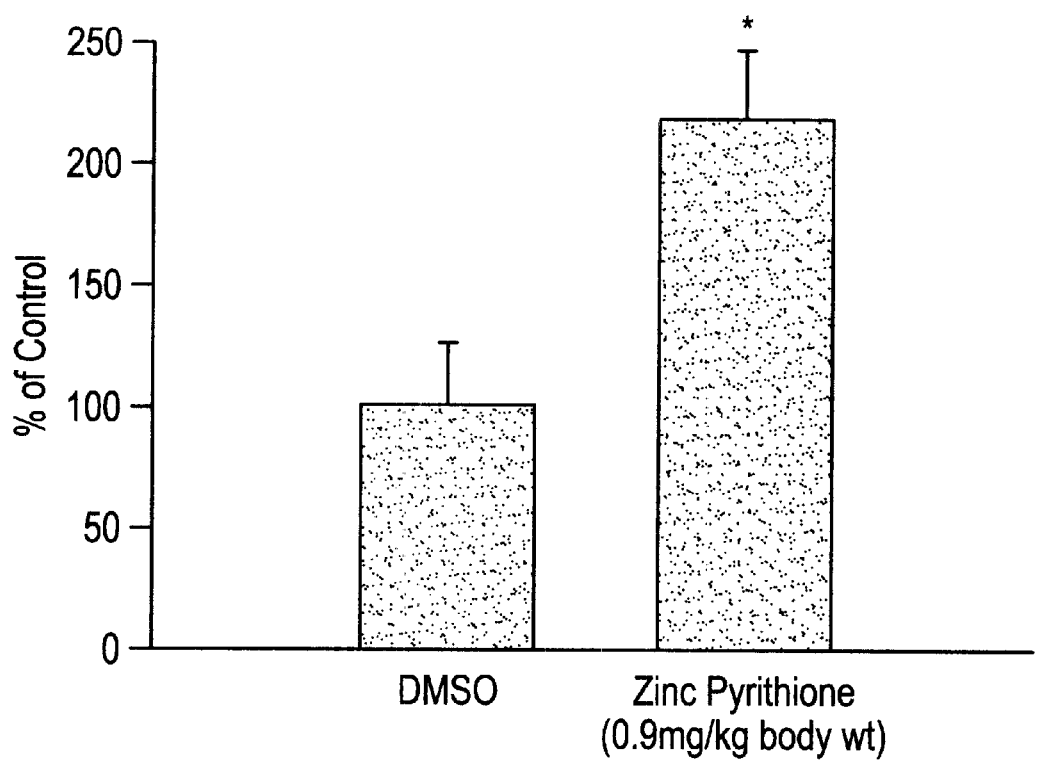
FIG. 2 shows the effects of zinc pyrithione on HSP-70 in heart.

Western blot analysis revealed that zinc-pyrithione (0.9 mg/kg body weight) significantly increased the intracellular content of Heat Shock Protein 70 (HSP70) in the ischemic myocardium (FIG. 2). The content of the HSP70 in the ischemic myocardium was determined using standard immunoblotting techniques. The heart tissue was homogenized on ice for 45 s using a Polytron homogenizer at 10,000 rpm in 8 volumes of 10 mM HEPES (pH 7.9), containing 10 mM KCl, 1.5 mM $MgCl_2$, 0.1% Nonidet P-40, 0.5 mM DTT, 0.5 mM PMSF, 0.5 mM spermidine, 0.15 mM spermine, 5 mg/ml aprotinin, 5 mg/ml leupeptin, and 5 mg/ml pepstatin. The homogenate was incubated on ice for 15 minutes and centrifuged at 35,000×g at 4° C. for 15 min. Aliquots (15 mg protein) of the supernatant were subjected to electrophoresis on 12% polyacrylamide gels and were transferred to polyvinylidene difluoride (PVDF) membranes. The membrane was incubated with a polyclonal rabbit antibody against HSP70, followed by goat anti-rabbit IgG conjugated to horseradish peroxidase (HRP). Protein band chemiluminescence was visualized on film according to manufacturer's instructions (NEN Life Science Products, Boston, Mass.), and was quantified with a densitometer and Molecular Analyst Software (Bio-Rad Laboratories, Hercules, Calif.). Since HSP70 has been shown to protect against apoptosis (Wong, H. R., et al. (1996) Am.J.Respir. Cell Mol.Biol. 15:745–751), and to be induced by zinc (Klosterhalfen, B., et al., (1997) Shock 7:254–262), the data suggest that zinc-pyrithione may exerts its protective effect by upregulating HSP70 synthesis. Zinc-pyrithione also caused a statistically significant decrease in the cytosolic concentration of PKC-α (data not shown), using the same method as that described for HSP70, with the exception that instead of using a polyclonal rabbit antibody against HSP70, we used an antibody against PKC-α. As PKC-α is a well known intracellular signalling agent, it was therefore concluded that $Zn^{2+}$ is capable of modulating intracellular signalling.

The limited amount of myocardial tissue available from these studies has not yet permitted the analysis of transcription factor activity in this tissue. However, analysis of brain tissue from the experimental rats by EMSA (electrophoretic mobility shift assays) showed strong effects on the nuclear content of the two transcription factors Sp1 and NF-kB. In the Electrophoretic Mobility Shift Assay (EMSA), brain samples were homogenized on ice using six slow strokes of a Teflon pestle homogenizer at 1000 rpm in 8 volumes of buffer containing 0.25 M sucrose, 10 mM HEPES, pH 7.6, 25 mM KCl, 1 mM EDTA, 10% glycerol, 0.15 mM spermine, and 0.5 mM spermidine. The homogenate was filtered through a 45 mm nylon sieve and layered over a 10 ml cushion of 2 M sucrose containing 10 mM HEPES, pH 7.6, 25 mM KCl, 1 mM EDTA, and 10% glycerol. The homogenate was centrifuged at 100,000×g at 4° C. for 1 h, the supernatant was discarded, and the pelleted nuclei were gently resuspended in 40 ml of a lysis buffer containing 20 mM HEPES, pH 7.9, 420 mM NaCl, 1.5 mM $MgCl_2$, 0.2 mM EDTA, 25% glycerol, 0.5 mM DTT, 0.5 mM PMSF, 0.5 mM spermidine, 0.15 mM spermine, and 5 mg/ml each of aprotinin, leupeptin and pepstatin. The suspension was incubated on ice for 45 min and centrifuged at 20,000×g at 4° C. for 10 min. The supernatant containing nuclear protein was collected and diluted 1:1 with a buffer containing 20 mM HEPES, pH 7.9, 50 mM KCl, 0.2 mM EDTA, 20% glycerol, 0.5 mM DTT, 0.5 mM PMSF, 0.5 mM spermidine, 0.15 mM spermine, and 5 mg/ml each of aprotinin, leupeptin and pepstatin. Protein concentrations were determined using the Bio Rad protein assay. For EMSA assays, double-stranded consensus oligonucleotides for NF-kB, AP-1 and Sp1 (Promega, Madison, Wis.) were radiolabelled with g[$^{32}$P] ATP (Amersham, Arlington Heights, Ill.).

Figure 3:
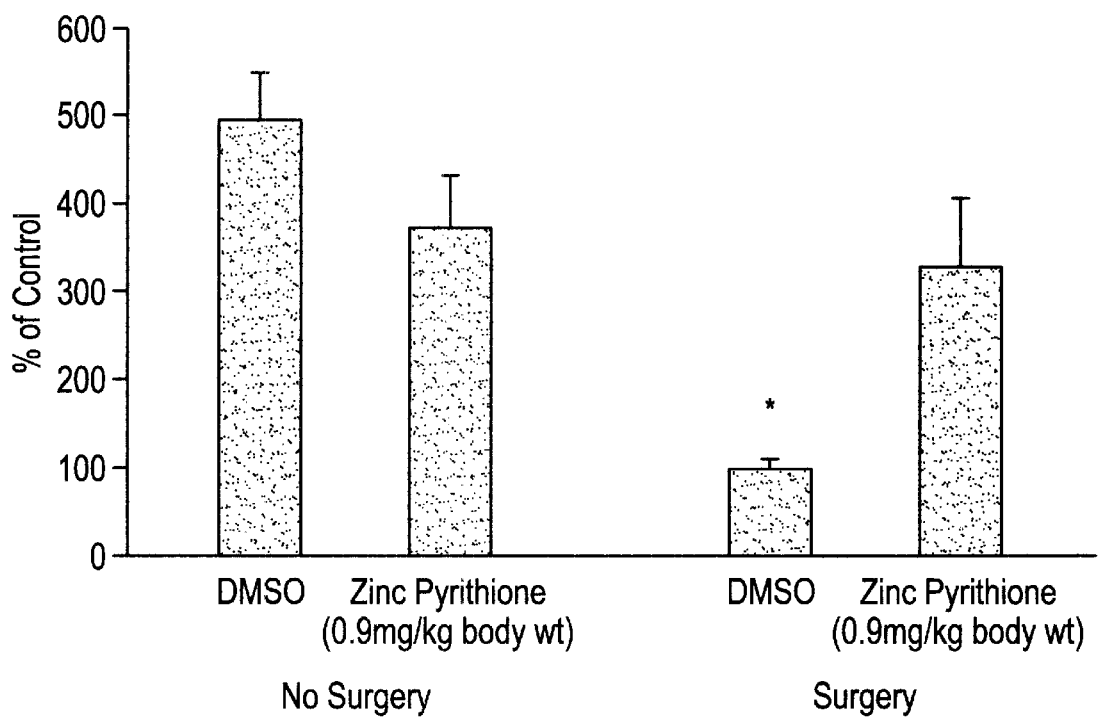
FIG. 3 shows the anti-apoptotic effect of zinc pyrithione on Sp1 in brain.
Figure 4:
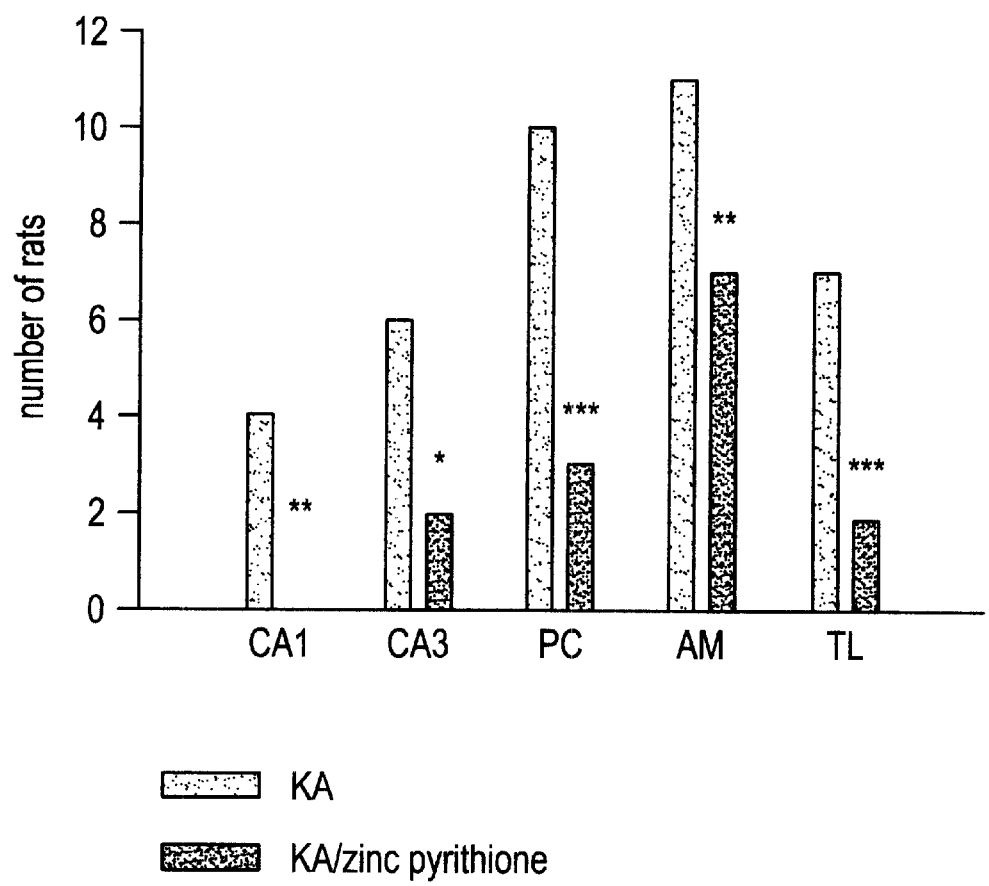
FIG. 4 shows the effects of zinc pyrithione on kainic acid induced damage in rat brain areas.

Five mg of nuclear protein were first incubated for 10 min at room temperature with 5 mg poly-d[I-C] (Boehringer Manheim, Montreal, Quebec) in DNA binding buffer (20 mM HEPES, pH 7.9, 0.2 mM EDTA, 0.2 mM EGTA, 100 mM KCl, 5% glycerol, and 2 mM DTT). Labeled probe (0.2 ng) was then added and the reaction mix incubated for a an additional 20 min in a final volume of 20 ml. The reaction mixture was subjected to electrophoresis on 5% polyacrylamide gel, and the dried gel was exposed to X-ray film. The intensity of the bands was quantitated with a densitometer and commercially available software (Molecular Analyst, Bio-Rad Laboratories, Hercules, Calif.). The subunit composition of NF-kB was determined with supershift assays. Antibodies (2 mg) to either p50 or p65 (Santa Cruz Biotechnologies, Inc. Santa Cruz, Calif.) were added to the incubation mixture and incubated for 20 min prior to the addition of poly-d[I-C]. No significant changes in the nuclear content of Sp1 were observed in control rats infused with zinc-pyrithione without coronary ligation, zinc-pyrithione strongly protected the brain tissue against the sharp decline in Sp1 caused by the ischemic episode (FIG. 3). Moreover, zinc-pyrithione significantly increased the level of NF-kB in the brain of rats subjected to myocardial ischemia, but had no effect on non-surgical control brains (data not shown). In view of the well established role of these transcription factors in apoptosis, our data suggest that zinc-pyrithione may protect against apoptosis in the heart by altering cell signalling and gene expression.

EXAMPLE 3
In Vivo Brain Model—Kainic Acid Injury.

Glutamate is the principal excitatory neurotransmitter in the brain, and plays a critical role in the etiology of different major brain pathologies such as cerebral ischemia, neurodegeneration, epilepsy, etc (Coyle, J. T. (1993) *Science* 262:689–695). Compounds which interact with the glutamate receptors are therefore important tools in the investigation of these diseases. Kainate is an excitotoxic glutamate analog that produces excessive neuronal excitation and seizures within hours following its intraperitoneal injection into adult rats. At 2–3 days after treatment, neurodegeneration can be observed in the limbic system in the form of apoptosis (Gillardon, F., et al., (1995) *Neurosci.Lett.* 192:85–88). Because the hippocampal subregions in the rat, particularly the CA3, are enriched in kainate receptors, they are particularly susceptible to kainate-induced neuronal death (Meldrum, B. S. (1994) *Neurology* 44:S14–S23). The neurotoxic effect of kainate in the rat hippocampal subregions involves a direct effect on presynaptic kainate receptors and an indirect effect on postsynaptic glutamate receptors due to the enhanced release of glutamate (Malva, J. O., et al., (1998) *Neurochem.Int.* 32:1–6). It appears likely that kainate-induced apoptosis is associated with the production of reactive oxygen intermediates (Hirata, H. et al., (1997) *Brain Res.Mol.Brain Res.* 48:145–148; Zhang, X., (1997) *Eur.J.Neurosci.* 9:760–769; Uz, T., et al., (1996) *Neuroscience* 73:631–636; Rong, Y. et al., (1996) *J.Neurochem.* 67:662–668), and the modulation of intracellular zinc (Cuajungco, M. P. et al., (1997) *Neurobiol.Dis.* 4:137–169).

Experimental Model:

The experimental approach utilized in these studies was the well-established model of neurotoxic injury in rat brains induced by kainic acid (KA). Male Wistar rats (250–350 g) were anesthetized with chloral hydrate (325 mg/kg). KA (10 mg/kg) was injected intraperitoneally. Zinc pyrithione in 1.2% DMSO in sterile water was injected intracerebroventricularly according to the following coordinates: AP −6.8, L +−1.5, DV +3.8 at the dose of 1 pmol/ventricle. Rats which did not receive zinc pyrithione were injected with 1.2% DMSO solution alone in water intracerebroventricularly. Zinc pyrithione was injected 15 min after KA administration. Sham operated rats received 1.2% DMSO in the lateral ventricles and isotonic saline intraperitoneally. The volume of substances injected into ventricles was 1.5 uL. Seizure activity in the rats was followed during first 4–6 h after KA administration. Gradation of KA-elicited limbic seizures was carried out according to accepted protocols (Rong, Y. et al., (1996) *J.Neurochem.* 67:662–668). Sham operated, KA-treated and KA/zinc treated rats were decapitated after 1–3 days. The brains were removed, fixed in AFA, paraffin embedded, sectioned (10 μm) and stained by the Nissl method, using routine methodology.

Figure 6:
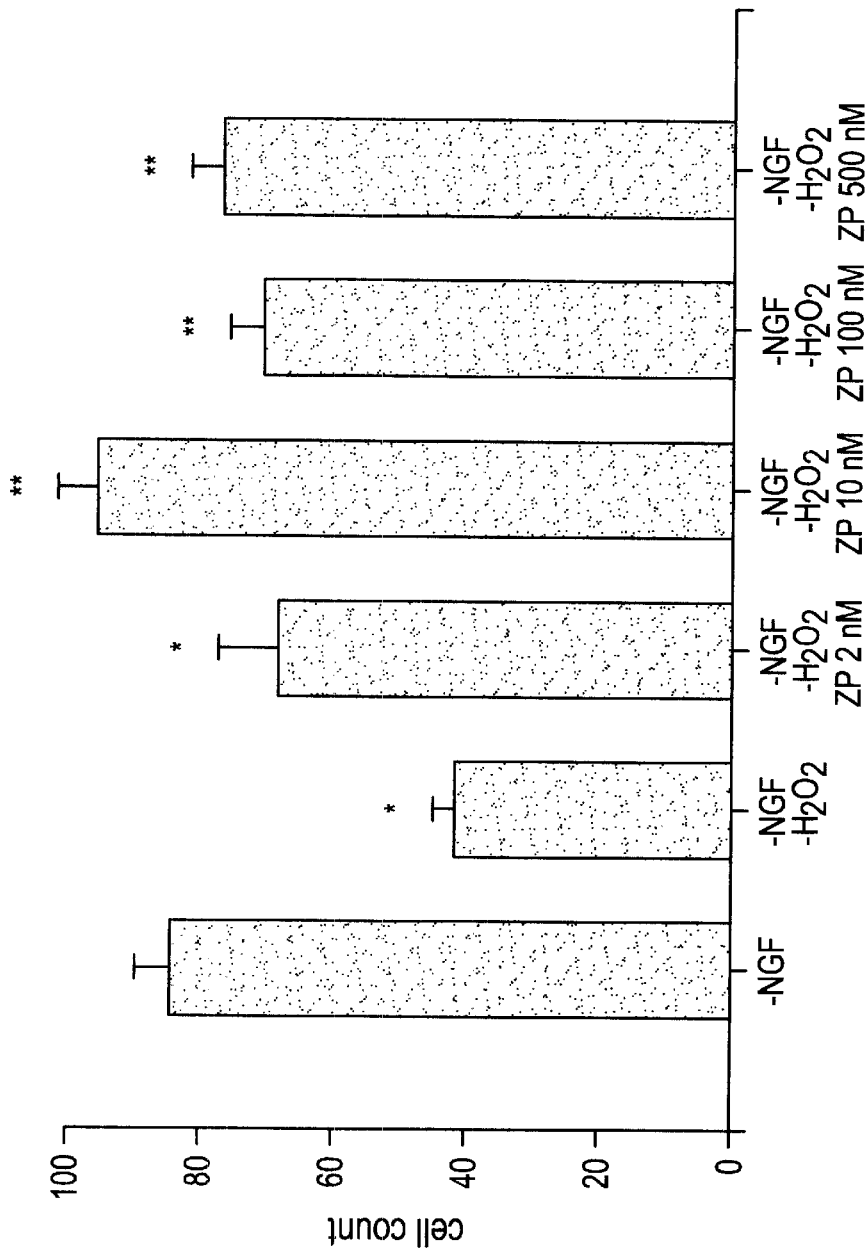
FIG. 6 shows the protective effects of zinc pyrithione in PC12 cells subjected to oxidative stress.

Results:

Brains of sham-operated rats and control animals injected icv with zinc-pyrithione did not show any obvious damage in any brain region. However, administration of KA caused neuronal degeneration and cell loss in a number of brain regions, with injury reaching maximal levels within the first day after KA treatment. Preliminary data suggest that the brain damage is attributable to apoptosis, as detected by the TUNEL stain (not shown). Twelve rats were subjected to treatment alone and 12 were treated with KA followed by zinc-pyrithione. FIG. 6 shows the number of rats (out of 12) that displayed detectable signs of injury in each group. The extent of injury in tissue sections was determined by thorough histological examination, comparing gross anatomical features, the number of visible, intact nuclei in each region, and the presence of other obvious signs of tissue injury. Reproducible and pronounced damage was seen in the hippocampal subregions CA1 and CA3, the pyriform cortex (PC), amygdalar region (AM), and thalamus (TL) in the KA-treated group (FIG. 6). However, icv administration of zinc-pyrithione provided statistically significant protection in all regions with the exception of CA3, where only a protective trend was observed (*, $P<0.1$ (trend); , $P<0.05$; *, $P<0.01$, Fisher's exact test).

Figure 5:
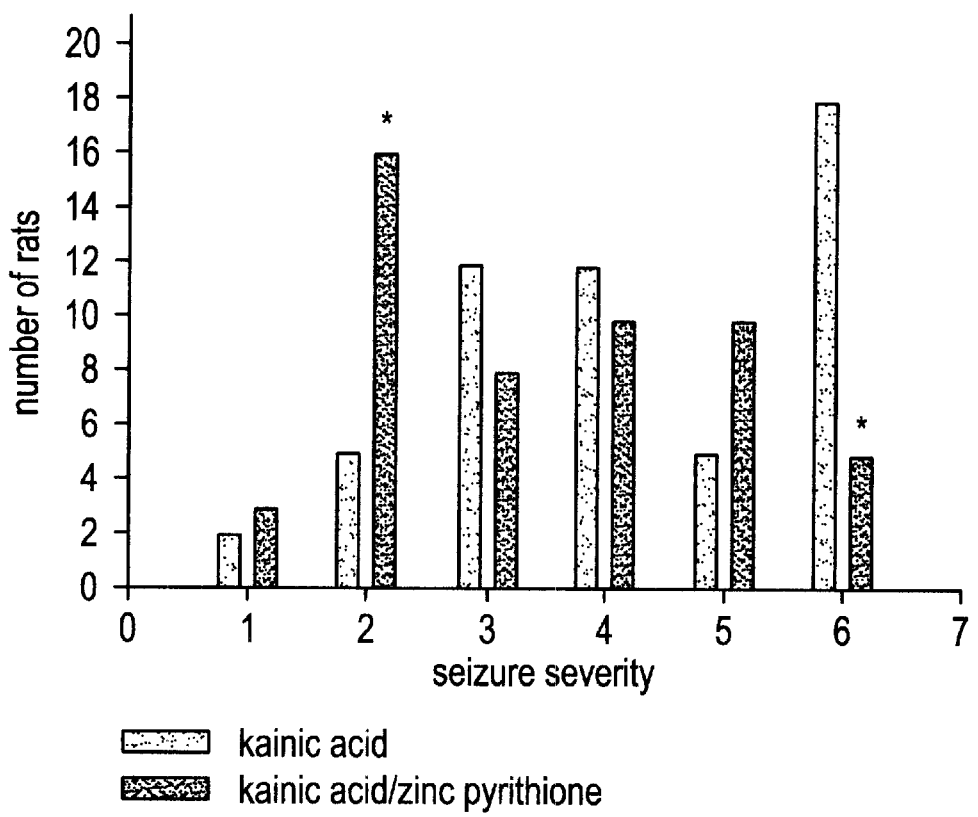
FIG. 5 shows the effects of zinc pyrithione on the severity of kainic acid induced seizures in rats.

Zinc-pyrithione also changed the pattern of KA-induced seizures in the rats. The seizure study was performed with 57 rats in the KA-alone group, and 58 in the KA plus zinc-pyrithione group. The data presented in FIG. 5 show the number of rats in which a given seizure severity was the final stage of severity observed. Notably, zinc-pyrithione caused a statistically significant 3.2-fold decrease in the incidence of the most severe and irreversible stage of seizures ("jumping", stage 6). In other words, of the 57 rats treated with KA alone, fully 18 reached the lethal stage 6, as compared with only 5 out of 58 in the KA plus zinc-pyrithione group. The data further show that the final stage of severity tended to be much lower in the zinc-pyrithione group, as illustrated by the 3.2-fold increase in the number of zinc-pyrithione treated rats at level 2 ("wet dog shake" stage). (*, P<0.01, Fisher's exact test). In summary, zinc-pyrithione significantly decreased KA-induced cell death in a number of brain regions, and significantly lowered the severity of KA-induced seizures in rats.

Effect of Zinc Ionophores on the Subcutaneous PTZ Test in Rats

The subcutaneous PTZ (pentylenetetrazole) test in rodents is commonly used to identify compounds capable of raising seizure threshold (White at al., *Adv. Neurol.*, 76:29–39, 1998). The ability of a test compound to inhibit PTZ-induced clonic and tonic convulsions is currently regarded as predictive of efficacy against "absence" seizures and/or myoclonic seizures (Suzdak, Jansen, 1995, *Epilepsia*, 36(6):612–626). The pharmacological profile of the PTZ test varies depending on the endpoint selected: PTZ can produce myoclonic jerks, repeated clonic seizures of forelimbs and hindlimbs with and without loss of righting reflex, and loss of righting reflex followed by tonic extension of the forelimbs and hind limbs. To have the full picture of the PTZ-induced seizures and of the effects of zinc ionophores, and to make the model more discriminative (White at al., supra) the behavioral reaction of each rat was monitored for a period of 2 hours which is much longer than the usual time period in conventional screening experiments.

Figure 7:
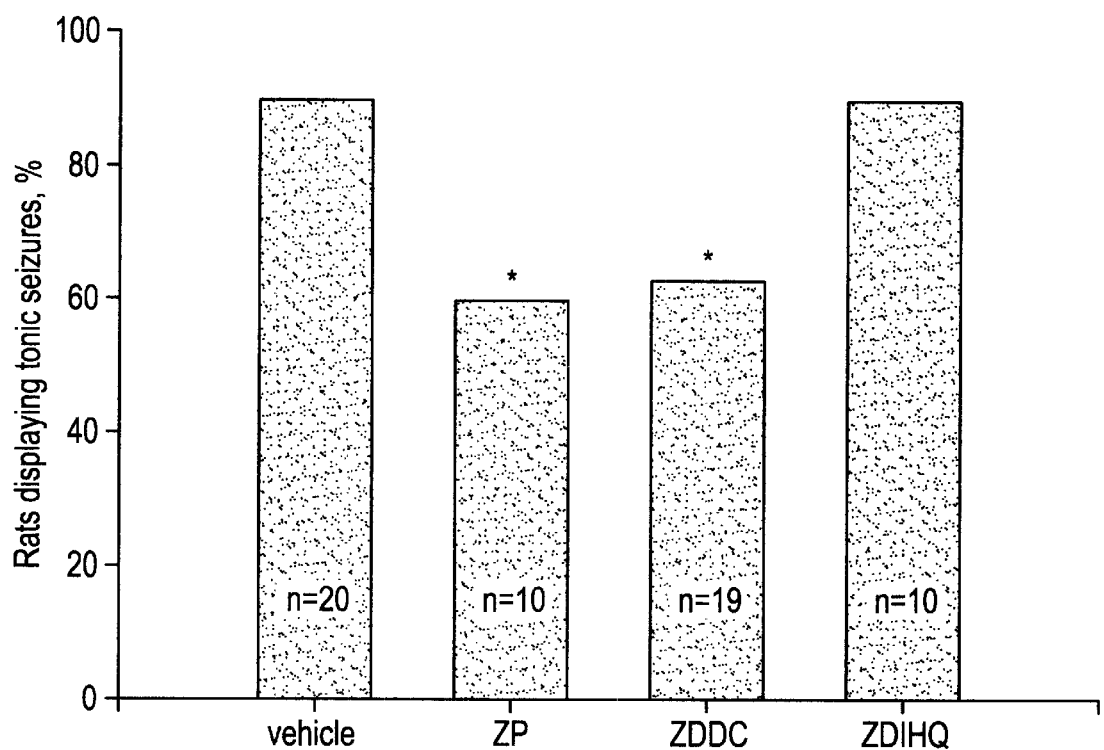
FIG. 7 shows the effects of zinc ionophores on the number of rats with tonic seizures.
Figure 8:
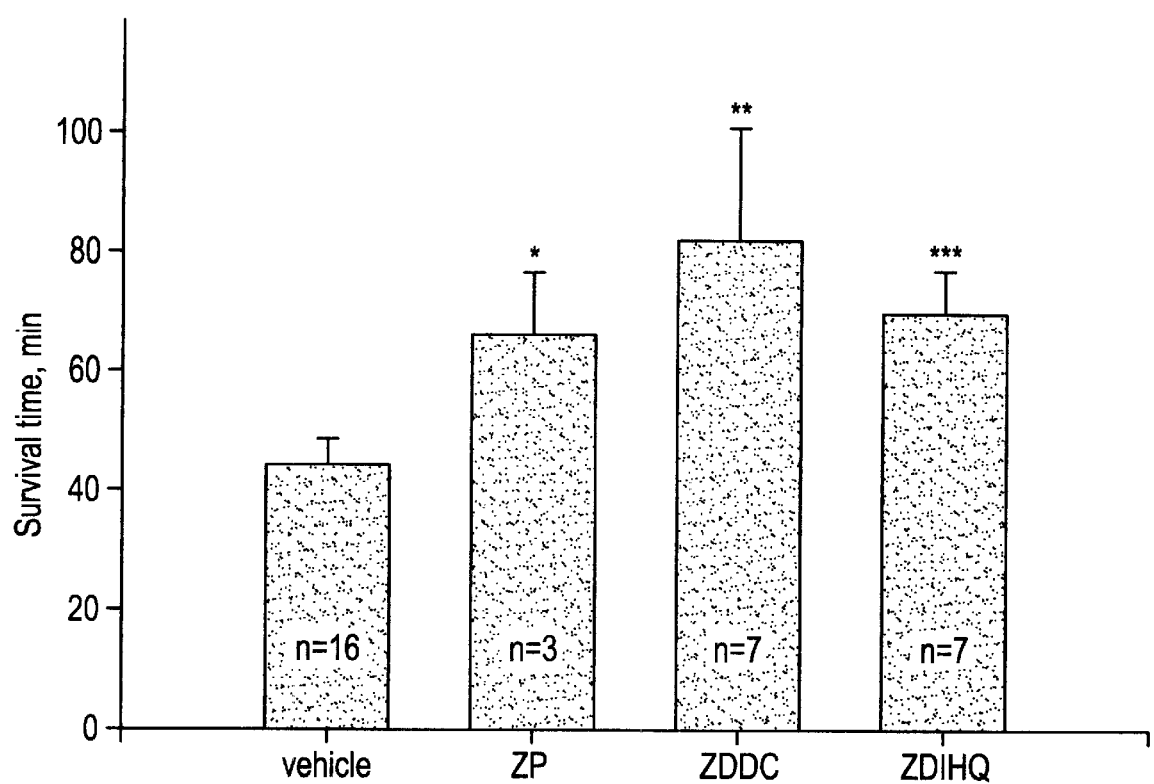
FIG. 8 shows the effects of zinc ionophores on the mortality in the sc PTZ test.

PTZ (120 mg/kg) was administered subcutaneously to male Wistar rats (300–450 g). Zinc ionophores were injected i.p. in one bolus, 30 min before PTZ at a dose of 62.5 nmol/kg and a total volume of 0.25–0.4 ml. The following groups were studied: vehicle (2.5% DMSO) n=20; zinc pyrithione (ZP, 19.9 $\mu$g/kg) n=10; zinc diethyldithiocarbamate (ZDDC, 22.5 $\mu$g/kg) n=19; and zinc 5,7-diiodo-8-hydroxyquinoline (ZDIHQ, 53.7 $\mu$g/kg) n=10. Two of the three zinc ionophores studied, ZDDC and ZP, significantly decreased mortality in the PTZ model from 80% to 37% and 30%, respectively (FIG. 7). ZDDC and ZP also significantly decreased the number of rats displaying the most severe tonic seizures from 90% to 63% and 60%, respectively (FIG. 8).

Kruskal-Wallis ANOVA showed a highly significant dependence of survival time on zinc ionophores administration (Chi square=16.7; P<0.001). For those rats which died within 2 h ("non-survivors"), the mean time to death increased significantly with all three ionophores. The survival time increased by 1.5, 1.9, and 1.6 fold for ZDDC, ZP, and ZDIHQ, respectively. Thus, zinc ionophores not only decreased the PTZ-induced mortality, but also increased the survival time of the non-survivors. Since tonic seizures are believed to be closely related to mortality from seizures, the decrease in their incidence after ZP or ZDDC injections may be one of the reason for higher survival in these groups.

The latency of the onset of clonic and tonic seizures is a good index of the anti-epileptic potential of the tested substances. The ionophore data are presented in Table 2. All groups administered ionophores showed longer mean latencies for all seizure types and a statistically significant difference was obtained for the latency of tonus for ZDIHQ. Statistical trends were observed with ZDDC and ZDIHQ for the increase in latencies for clonic seizures, and with ZDIHQ for the tonic seizures. It should be noted that since tonic seizures are the most severe form of seizure and in most cases lead to death, the observed delay in tonic seizures is highly significant.

TABLE 2

Effects of zinc ionophores on latencies of different seizure types (min, M ± S.E.M.).

| Group | Clonus without loss of righting reflex | Clonus with loss of righting reflex | Tonic seizure |
|---|---|---|---|
| Vehicle | 13.3 ± 1.1 | 15.8 ± 1.5 | 20.3 ± 1.7 |
|  | n = 20 | n = 19 | n = 18 |
| ZP | 14.3 ± 1.8 | 16.8 ± 3.2 | 24.5 ± 5.5 |
|  | n = 10 | n = 9 | n = 6 |
| ZDDC | 17.2 ± 1.6 | 18.5 ± 2.0 | 25.5 ± 3.1 |
|  | n = 19; P < 0.06 | n = 16 | n = 12; P = 0.1 |
| ZDIHQ | 15.6 ± 1.7 | 21.2 ± 2.7 | 28.4 ± 4.1 |
|  | n = 10 | n = 10; P < 0.07 | n = 9; P = 0.04 |

P values vs. vehicle (T-test) are presented.

The data show that all three zinc ionophores are effective in blocking the effects of PTZ, although their beneficial effect varied with respect to different parameters of the PTZ-induced pathology. ZP and ZDDC significantly decreased mortality and the incidence of tonic seizures, whereas ZDIHQ delayed tonic seizures. All ionophores increased survival time.

Effects of Zinc Pyrithione in Audiogenic Epilepsy Model in Rats

Acoustic induction of seizures in rodents is a model of generalized tonic-clonic limbic seizures induced by sudden exposure to high intensity sound of up to 100–110 dB. This assay is normally performed in genetically susceptible strains of rat (Garcia-Cairasco et al., (1993), *Behav. Bran. Res.*, 58(1–2):57–67; 1998; Zivanovic et al., (1998), *Pharmacol. Res.*, 38(5):347–351), or in susceptible animals which are identified by screening large populations of rats. The latter approach was employed by the present inventor.

Male Wistar rats (250–350 g) susceptible to audiogenic epilepsy were identified by screening 200 rats. Animals that developed seizures in response to a 60 dB sound were selected for future testing (40 rats, 20% of the overall population). From this group of susceptible rats, only 21 rats that displayed reproducible seizures over a span of 3 weeks when stimulated once every 5–7 days were selected for the study. The reproducibility of the audiogenic response in these rats meant that each rat could serve as its own control in these studies.

The studies were conducted as follows: each of the 21 selected rats was administered in the subsequent weeks either vehicle alone, or ZP, or no injection, in a random, blinded fashion, and the response to sound stimulation was recorded. ZP (36 $\mu$g/kg) was administered 30 min before the acoustic stimulation using a bolus intravenous injection of ZP in saline containing 2.5% DMSO in a total volume of 0.2–0.4 ml. The vehicle-alone group received only 2.5% DMSO. Control animals did not receive any injection. Following two weeks of behavioral tests during which seizure susceptibility was determined, electrodes were implanted in the motor cortex of selected rats and EEG records were obtained before and after audiogenic stimulation, as well as before and after i.v. injection of ZP. The EEG studies aimed to examine the possible correlation between the anti-epileptic effects of ZP at the behavioral level and brain activity level. The scale used to classify decreasing seizure severity was as follows: stage 1—wild running; stage 2—clonic seizures without loss of righting reflex; and stage 3—clonic seizures with the loss of righting reflex. The sound intensity used in these studies (60 dB) was relatively mild, and did not cause tonic seizures or mortality in the test animals.

Figure 9:
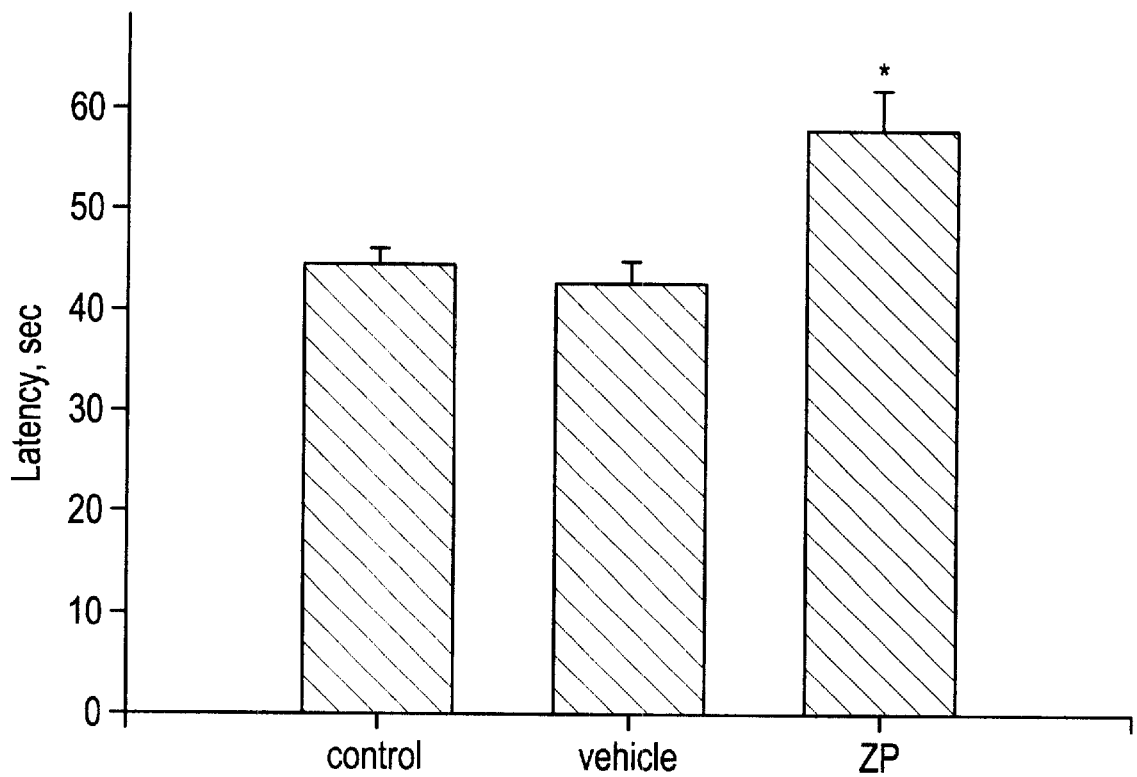
FIG. 9 shows the effect of zinc pyrithione on latency of audiogenic seizure onset.
Figure 10:
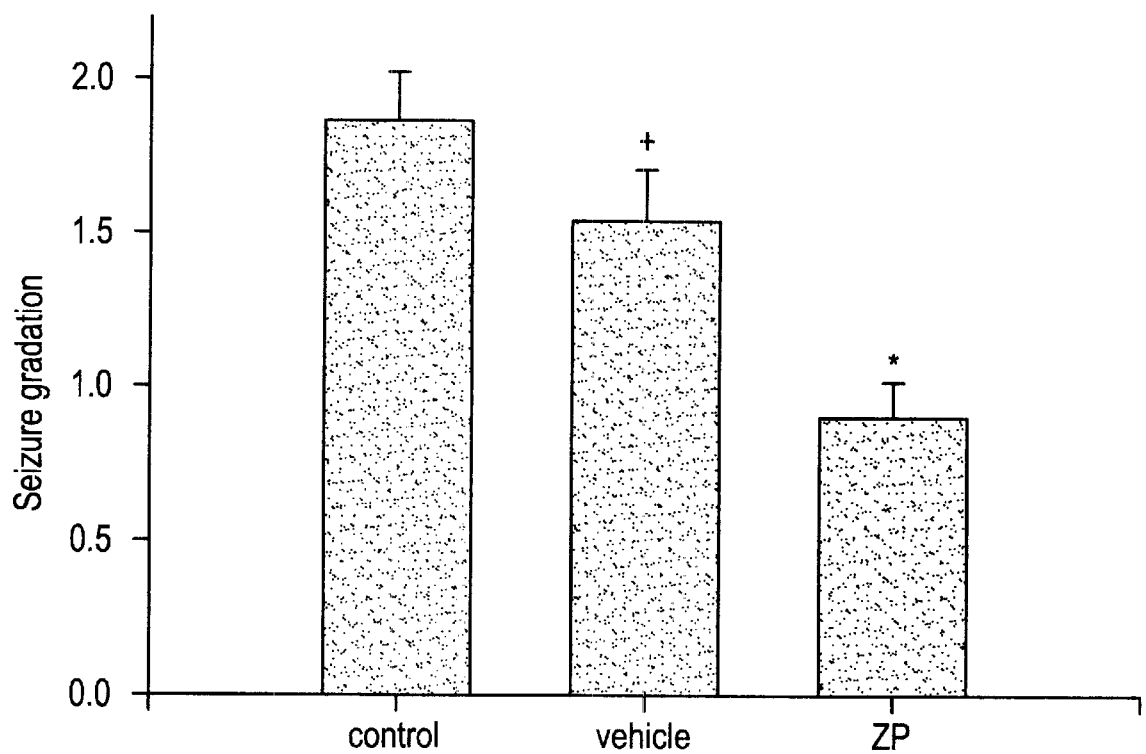
FIG. 10 shows the effect of zinc pyrithione on seizure severity in the audiogenic epilepsy.

The data show that ZP delayed the onset of audiogenic seizures, increasing the latency period by 36% from 42.7±2.2 s (vehicle) to 58.1±3.9 s (FIG. 9) and decreasing the severity of seizures by 41% from 1.55±0.15 (vehicle) to 0.91±0.11 (FIG. 10). ANOVA showed a strong dependence of seizure parameters on the injectate (control, vehicle, ZP): for latency F=9.37, P=0.0003; for seizure severity F=11.74, P=0.00005. Post-hoc comparisons using the Duncan test showed a significant difference between the ZP group and vehicle (P=0.0003 for latency, and P=0.002 for seizure severity). The post hoc test did not show a significant difference between vehicle (DMSO) and control groups. The data therefore demonstrate a highly significant protective effect by ZP in the audiogenic seizure model in Wistar rats, showing both an increase in latency and a decrease in seizure severity.

Of the 21 rats used in this study, ZP decreased the seizure level in 52%. In comparison to vehicle alone, ZP significantly increased the number of rats which showed resistance to the audiogenic stimulus, preventing seizures in fully 19% of the rats (P<0.05; Chi-square test). ZP also decreased the fraction of rats displaying clonic seizures from 48% to 14% (P<0.05; Chi-square test), shifting the seizure profile to the less severe levels. Thus, the data show a clear delay in the time to seizure onset, as well as a reduction in seizure severity, as a result of ZP administration.

The basal EEG's of the rats displayed a variety of epi-signs: peaks, sharp waves, and peak-waves. Sound-induced seizure was preceded by an increase in the incidence of peak groups and other epi-signs (motor excitation produced some artifacts on the EEG). Injection of ZP before the sound stimulation decreased the incidence of peaks and other epi-signs in the basal EEG and produced a regular theta-rhythm, with only single peaks evident in the EEG. Audiogenic stimulation 15–30 min after ZP injection induced the appearance of a regular theta-rhythm, an EEG correlate of a normal arousal reaction to the sound stimulation. Though some peaks were still evident, the clear dominance of theta-rhythm (which was absent when only vehicle was injected) indicated a normalization of the EEG. Thus, the seizure and EEG data demonstrates a decrease in sound-induced seizure activity, confirming an anti-epileptic activity by zinc pyrithione.

EXAMPLE 4
In Vitro Neuronal Cell Model—Oxidative Stress

Oxidative stress is believed to play an important role in the apoptotic neuronal cell death associated with many different neurodegenerative conditions (e.g., Alzheimer's disease, Parkinson's disease, cerebral ischemia, etc.) (Jenner, P. (1994) *Lancet* 344:796–798). The non-differentiated rat pheochromocytoma PC12 cells are a cell line which differentiates to a neuronal cell type in the presence of Nerve Growth Factor (NGF), but undergoes apoptotic cell death when deprived of NGF. These cells also undergo apoptotic cell death when exposed to oxidants such as hydrogen peroxide (Satoh, T., et al., (1997) *J.Neurosci.Res.* 50:413–420; Maroto, R. et al., (1997) *J.Neurochem.* 69:514–523; Kubo, T., et al., (1996) *Brain Res.* 733:175–183). PC2 cells are therefore a useful cell model with which to analyze the molecular mechanisms of apoptosis induced by oxidative stress and other stimuli in neuronal cells (Kubo, T., et al., (1996) *Brain Res.* 733:175–183, incorporated herein by reference).

Experimental Model:

PC12 cells were seeded on coverslips covered with poly-L-lysine in 24-well plates, and were grown in RPMI-1640 containing 10% FCS, 5% horse serum, 2 mM glutamine, and 40 mg/kg gentamicin in 5% $CO_2$ at 37° C. RPMI-1640 medium containing 1% serum (embryonal calf and horse serum, 2:1) and 50 ng/ml NGF was used to induce differentiation. Differentiated PC12 monolayers were washed and were induced to undergo apoptosis in two ways: a) incubation for 4 h with normal growth medium without serum or NGF, and b) incubation for 4 h with normal growth medium (plus serum and NGF) containing 20 $\mu$M hydrogen peroxide ($H_2O_2$). The protective effect of zinc-pyrithione against both types of apoptosis was tested by preincubating the cells with this compound for only 5 minutes immediately prior to initiating apoptosis-inducing treatments a or b. Control cells were pretreated with the carrier DMSO alone. Pretreatment with zinc-pyrithione, rather than the more relevant post-treatment approach, was used in this model because of practical experimental considerations. However, the close temporal proximity of the pretreatment to the initiation of the injurious treatment is more representative of a concomitant exposure of the cells to both zinc-pyrithione and the injurious agent, rather than an authentic pretreatment. At the end of the 4 h incubation, the cells were fixed with methanol:acetone (1:1) at −20° C. and were stained with Hoechst 33258 to visualize the nuclei.

Results:

The data show that zinc-pyrithione (2–500 nM) provided statistically significant protection against $H_2O_2$-induced apoptosis, with 10 nM being the optimal concentration (FIG. 6). Compared to control cells (+NGF), treatment with $H_2O_2$ resulted in the loss of approximately 50% of the cells through apoptosis (+NGF, +$H_2O_2$). However, treatment with as little as 2 nM zinc-pyrithione for 5 min significantly attenuated cell death. (*, P<0.005 vs. +NGF; +, P<0.05 vs. NGF+$H_2O_2$; ++, P<0.02 vs. NGF+$H_2O_2$, Mann-Whitney test, n=4).

Figure 11:
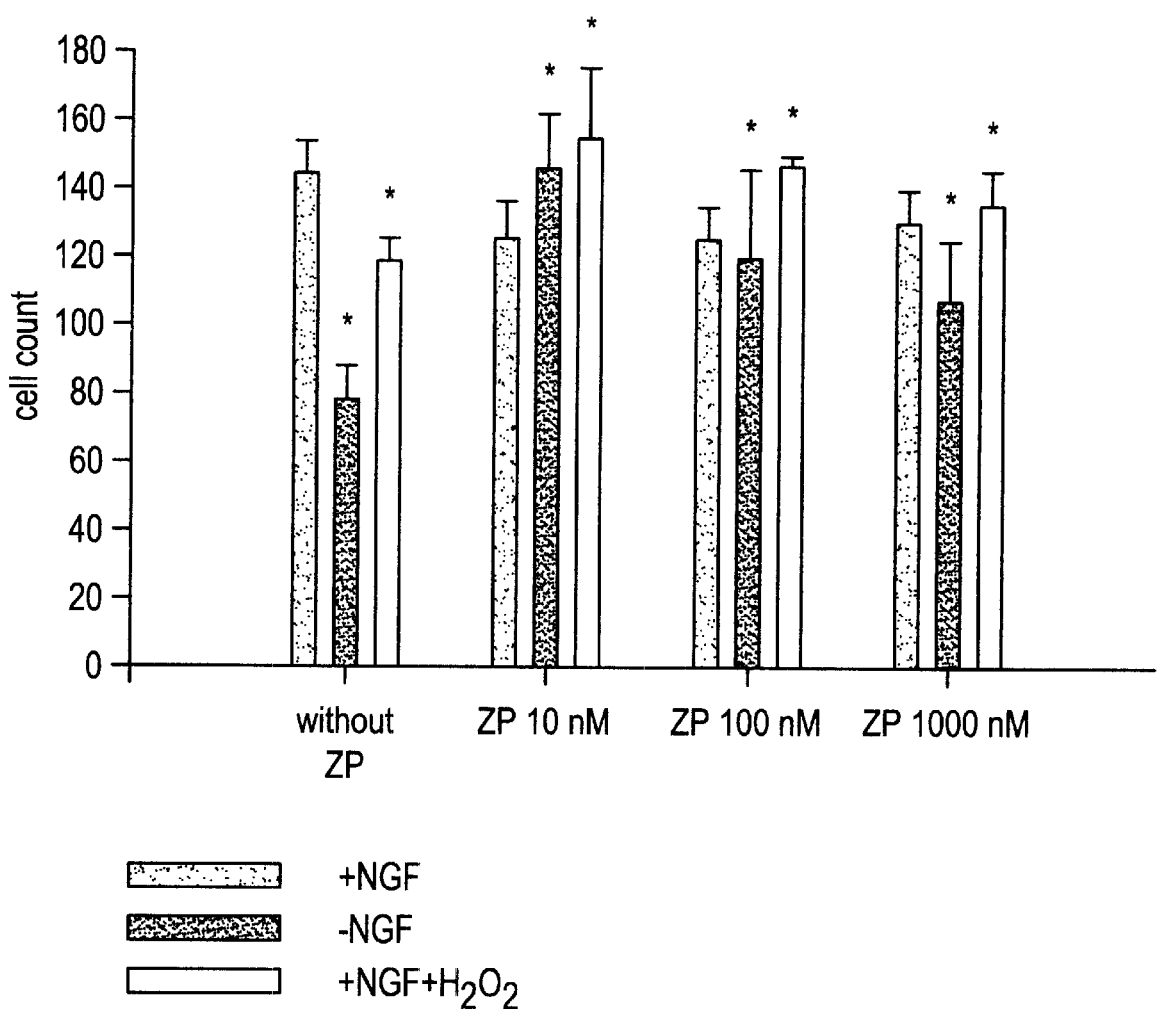
FIG. 11 shows the protective effects of zinc pyrithione in PC12 cells.

In another series of tests (FIG. 11), the ability of zinc-pyrithione to protect against $H_2O_2$ was confirmed, and also demonstrated that this compound can block the apoptosis caused by serum and NGF deprivation. Here too 10 nM appeared to be the optimally protective concentration of zinc-pyrithione. Zinc-pyrithione at concentrations as high as 1000 nM did not show any effects on cell growth in control cultures. (*, P<0.05 vs. +NGF; +, P<0.05 vs. respective "without ZP" group, Mann-Whitney test, n=3). The addition of $Zn^{2+}$ alone, at concentrations equivalent to those of zinc-pyrithione, to $H_2O_2$-treated cells did not block apoptosis (not shown), suggesting that the ionophore pyrithione is necessary for the transport of $Zn^{2+}$ into the cytosol, and that it is this intracellular $Zn^{2+}$ which accounts for the protective effects of zinc-pyrithione.

EXAMPLE 5
In Vitro Endothelial Model—Response to Ionizing Radiation and TNFα

Ionizing radiation has been shown to induce apoptosis in a variety of cell and tissue types (Van Antwerp, D. J., et al. (1996) *Science* 274:787–789; Findik, D., et al., (1995) *J.Cell.Biochem.* 57:12–21) including endothelial cells (Langley, R. E., et al. (1997) *Br.J.Cancer* 75:666–672). Although the mechanisms by which ionizing radiation induces apoptosis have yet to be resolved, it has been shown to directly induce DNA damage, to generate the formation of reactive oxygen species and to alter membrane structure (Datta, R., et al. (1997) *J.Biol.Chem.* 272:1965–1969), all of which can contribute to apoptotic cell death.

One well established effect of ionizing radiation is its alteration of gene transcription by means of the modulation of transcription factors. For example, radiation has been shown to induce the activation of the transcription factor NF-kB in several cell types (Valerie, K., et al., (1995) *Biochemistry* 34:15768–15776), including endothelial cells (Hallahan, D. et al., (1995) *Biochem.Biophys.Res.Commun.* 217:784–795). The cytokine TNFα is also capable of causing apoptosis in endothelial cells either alone (Slowik, M. R., et al., (1997) *Lab.Invest.* 77:257–267; Spyridopoulos, I., et al., (1998) *Circulation* 98:2883–2890) or synergistically with other agents (Eissner, G., et al., (1995) *Blood* 86:4184–4193). Here too, the apoptotic events are heavily regulated by alterations in transcription factor activity (Hu, X. L., (1998) *Blood* 92:2759–2765). The studies performed with this model were designed to examine the ability of zinc-pyrithione to block radiation-induced apoptosis, and to elucidate the effect of zinc-pyrithione at the transcriptional level in response to either ionizing radiation or TNFα.

Experimental Model:
Cell Culture:

Human umbilical vein endothelial cells (HUVEC) were purchased from Clonetics (San Diego, Calif.) and used from passages 2–4. Cells were cultured on gelatin-coated culture dishes in Endothelial Basal Medium (Clonetics) supplemented with 10 ng/ml human recombinant epidermal growth factor, 1.0 ug/ml hydrocortisone, 50 ug/ml gentamicin, 50 ng/ml amphotetericin B, 12 ug/ml bovine brain extract and 2% v/v fetal bovine serum, in a humidified chamber at 37° C. and 5% $CO_2$. To maintain cell populations, proliferating HUVEC were passaged at 80–90% confluency.

Experimental Treatments:

HUVEC were grown to confluency, and then given an additional 24 hours to achieve quiescence prior to experimental treatment. The following treatments were performed:

Radiation:

The cells were washed twice with 37° C. D-PBS and then irradiated in fresh media. Irradiated cells received a dose of 1000 Rads of gamma-irradiation from a $^{137}$Cesium source (Atomic Energy of Canada). The cells were then incubated for 2 hours (cytosolic and nuclear protein extraction) or 8 hours (Hoechst staining and DNA electrophoresis).

TNFα:

The cells were washed twice with 37° C. D-PBS and then incubated in media containing the TNFα (20 ng/ml, from a stock of 10 ug/ml prepared in phosphate buffered saline (PBS)-1%bovine serum albumin. Control cells received fresh media alone. The cells were then incubated for 2 hours (cytosolic and nuclear protein extraction) or 8 hours (Hoechst staining and DNA electrophoresis).

Hoechst Staining:

Cells were grown on round, gelatin coated 12 mm glass coverslips, and following treatment, were fixed with 0.5 ml of 1% glutaraldehyde in PBS for 10 minutes at room temperature (RT). The cells were then washed twice with PBS for 5 minutes, and permeabilized with 0.5 ml of 1:1 methanol/acetone for 10 minutes at RT, followed by two five minute PBS washes. The cells were then incubated with Hoechst 33258 (bis-benzimide, 0.05 mg/ml in $H_2O$), a fluorescent DNA binding dye, for 30 minutes at room temperature, in the dark. The nuclear morphology of the cells was then visualized under a Zeiss Axiophot fluorescence microscope.

Preparation of Cytosolic and Nuclear Extracts:

Cells were grown on 100 $mm^2$ culture dishes, and following treatment, were scraped into ice cold PBS and collected by centrifugation at 200×g for 5 minutes. The cells were then resuspended and washed once in 1 ml of ice cold PBS and centrifuged at 200×g for 5 minutes at 4° C. The cells were resuspended in 1 ml of Buffer A (10 mM HEPES, 10 mM KCl, 1.5 mM MgCl2, pH=7.9, 1.5 mM DTT and 0.5 mM phenyl methyl sulphonyl fluoride (PMSF)) and centrifuged at 200×g for 5 minutes at 4° C. The cells were then resuspended and lysed in 300 ul of Buffer A containing 0.1% Nonidet P-40 for 25 minutes on ice. The homogenate was then spun at 20,000×g for 10 minutes at 4° C. The supernatant containing cytosolic proteins was combined with an equal volume of Buffer C (20 mM HEPES, 50 mM KCl, 1.0 mM EDTA, 0.1 MM EGTA, 20% glycerol, pH=7.9, 0.5 mM DTT and 0.5 mM PMSF) and was stored at –80° C. The pelleted nuclei were washed by resuspension in 1 ml of Buffer A and spun at 20,000×g for 1 minute. The supernatant containing residual cytosolic proteins was discarded and the pelleted nuclei were resuspended in 35 ul of Buffer B (20 mM HEPES, 420 mM NaCl, 1.5 mM $MgCl_2$, 0.2 mM EDTA, 25% glycerol, pH 7.9, 0.5 mM DTT, 0.5 mM PMSF, and the protease inhibitors spermidine, spermine, aprotinin, leupeptin and pepstatin) for 45 minutes on ice in order to extract the nuclear proteins. The nuclear extract was then obtained following centrifugation at 20,000×g for 15 minutes at 4° C., and was combined with an equal volume of Buffer C and stored at –80° C.

Determination of Protein Concentration:

The protein concentration in the nuclear and cytosolic extracts was determined using the Bradford Assay (Biorad) using bovine serum albumin as the standard.

Electrophoretic Mobility Shift Assay (EMSA):

Equal amounts of nuclear protein (5 ug) were incubated with poly dI–dC (5 ug from a stock of 2.5 ug/ul in TE buffer) for 10 minutes at RT. This reaction mixture was then incubated with 0.2 ng of 5' end-$^{32}$phosphorus-labelled double stranded oligonucleotide probe for 20 minutes at RT to allow the binding of nuclear proteins with the labeled probe. Loading buffer (5 ul of a mixture containing 20 mM HEPES, 100 mM KCl, 60% glycerol, 0.5 mM EDTA, 0.5 mM EGTA and 0.125% bromophenol blue) was added to the reaction mixture prior to the electrophoresis on a 5% native polyacrylamide gel. The gels were run in Tris-Glycine solution for 1.5 hours at 200V and were then dried between filter paper and cellophane for 1.5 hours at 80° C. under vacuum. The dried gels were exposed to X-ray film (Cronex) for up to 2 days at –80° C. For competition assays, the reaction mixture was incubated with a 125-fold excess of unlabeled probe for 20 minutes at RT prior to the addition of the labeled probe. For supershift assays, the reaction mixture was incubated with 2 mg of rabbit polyclonal anti-NFkB p50 or p65 antibody (Santa Cruz Biotechnology) for 20 minutes at RT immediately subsequent to the addition of the labeled probe. The bound antibody retards the mobility of the protein-DNA complex, resulting in a shifted band. The consensus oligonucleotides for the transcription factors NFkB (5'-ACT TGA GGG GAC TTT CCC AGG C-3'), AP-1 (5'-CGC TTG ATG AGT CAG CCG GAA-3') and Sp1 (5'-ATT CGA TCG GGG CGG GGC GAG C-3') (Promega) and were labeled as suggested by Promega with minor modifications. Briefly, oligonucleotides (20 ng), T4 Polynucleotide kinase and [g32P]ATP (60 uCi) were mixed in kinase buffer (50 mM Tris-HCl, pH 7.6, 10 mM $MgCl_2$, 5% glycerol and 5 mM DTT) and incubated at 37° C. for 1 hour. Labeled oligonucleotides were removed by centrifugation through a G-25 Sephadex Column at 8500rpm for 20 minutes. The labeled oligonucleotides were then diluted such that 2 ul of the probe mixture contained approximately 50000–100000 cpm.

Western Blotting:

Equal amounts of cytosolic protein (3 ug) were diluted 1:1 in sample buffer (0.125M Tris-HCl pH 6.8, 2.6% SDS, 125% glycerol, 0.1 ml beta-mercaptoethanol and bromo phenol blue). The mixture was placed in boiling water for 5 minutes to denature the proteins and was then subjected to SDS-PAGE for 2.5 hours at 100V in running buffer. The gels consisted of a stacking gel (4.5% acrylamide, 0.125M Tris-HCl pH=6.8, 0.1% SDS, 0.6% ammonium persulfate and 0.2% TEMED in $H_2O$) and a 10% running gel (10% acrylamide, 0.3% bis acrylamide, 8% glycerol, 0.375 Tris-HCl pH=8.8, 0.1% SDS, 0.04% ammonium persulfate and 0.05% TEMED in $H_2O$). After electrophoresis (100V, 50 minutes), the gels were equilibrated for 15 minutes in ice cold transfer buffer (25 mM Tris HCl, 20% methanol, and 192 mM glycine), then transferred onto a polyvinyllidene difluoride membrane for 1 hour at 100V. The blots were then blocked overnight in 5% skimmed milk in Tris-Buffered Saline containing 0.1% Tween-20 (TBS-T) at 4° C. with constant shaking. The blots were then washed with TBS-T and incubated for 1.5 hours in primary antibody (anti-IkBa, Santa Cruz Biotechnology) diluted 1:1000 in 2% skimmed milk in TBS-T and sodium azide at RT with constant shaking. The blots were then washed with TBS-T and incubated for 30 minutes in horseradish peroxidase labeled goat anti-rabbit IgG diluted 1:10000 in 2% skimmed milk in TBS-T at RT with constant shaking. Following treatment with the secondary antibody, the blots were extensively washed with TBS-T and incubated for 1 minute with chemiluminescent substrate. The blots were then exposed to X-ray film for 1–5 minutes.

Figure 12:
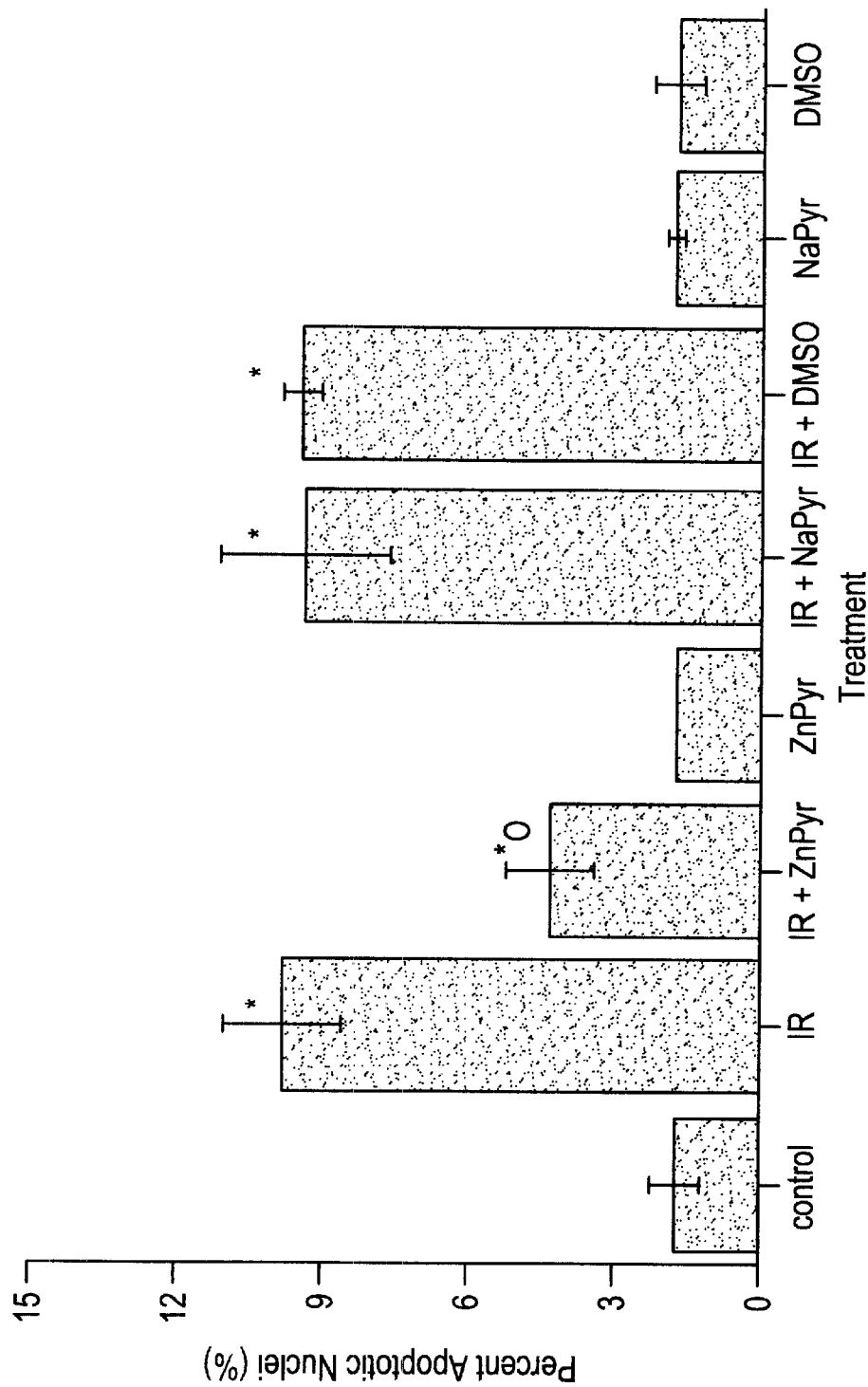
FIG. 12 shows the anti-apoptotic effect of zinc-pyrithione in irradiated human primary endothelial cells.

Results:

The data show protection by zinc-pyrithione against endothelial apoptosis, and also show that this protective effect is associated with transcriptional modulation. Treatment of irradiated HUVEC (IR) with zinc-pyrithione significantly blocked apoptosis (FIG. 12). The data also show that zinc is required for this effect since the sodium salt of pyrithione was not effective in preventing apoptosis. DMSO alone was also ineffective. No apoptosis was caused in control cultures by zinc-pyrithione, sodium-pyrithione, or DMSO alone (FIG. 12). (*, $P<0.05$ vs. Control; °, $P<0.05$ vs. irradiated cells, n=4).

Figure 13:
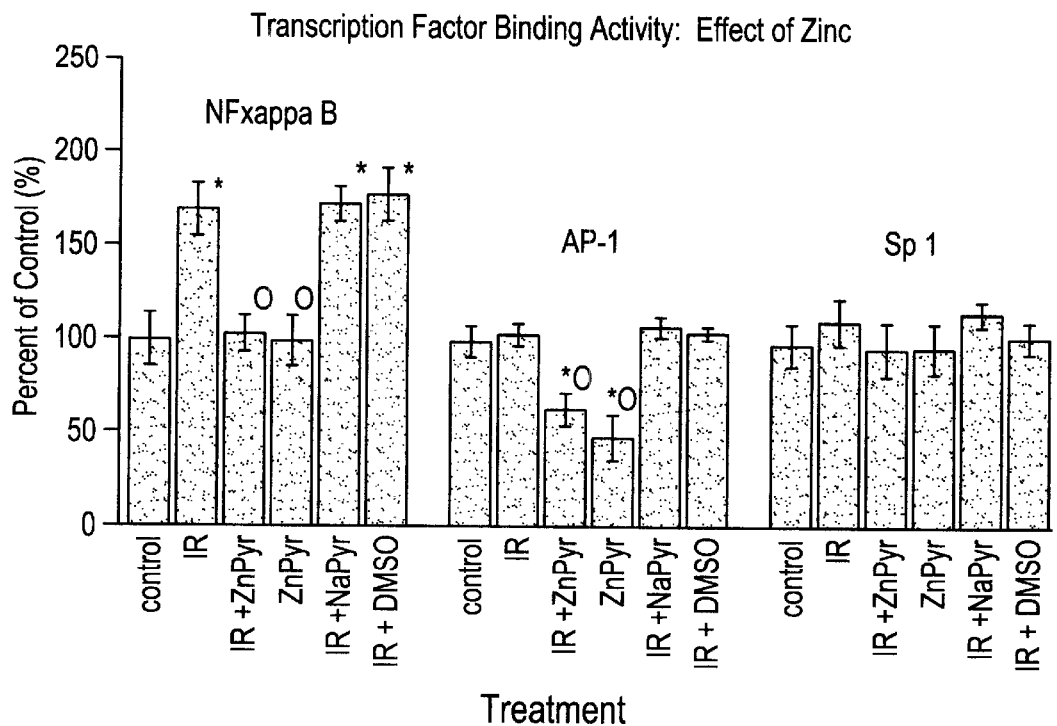
FIG. 13 shows the effects of zinc pyrithione on transcription factor binding activity in human primary endothelial cells.
Figure 14:
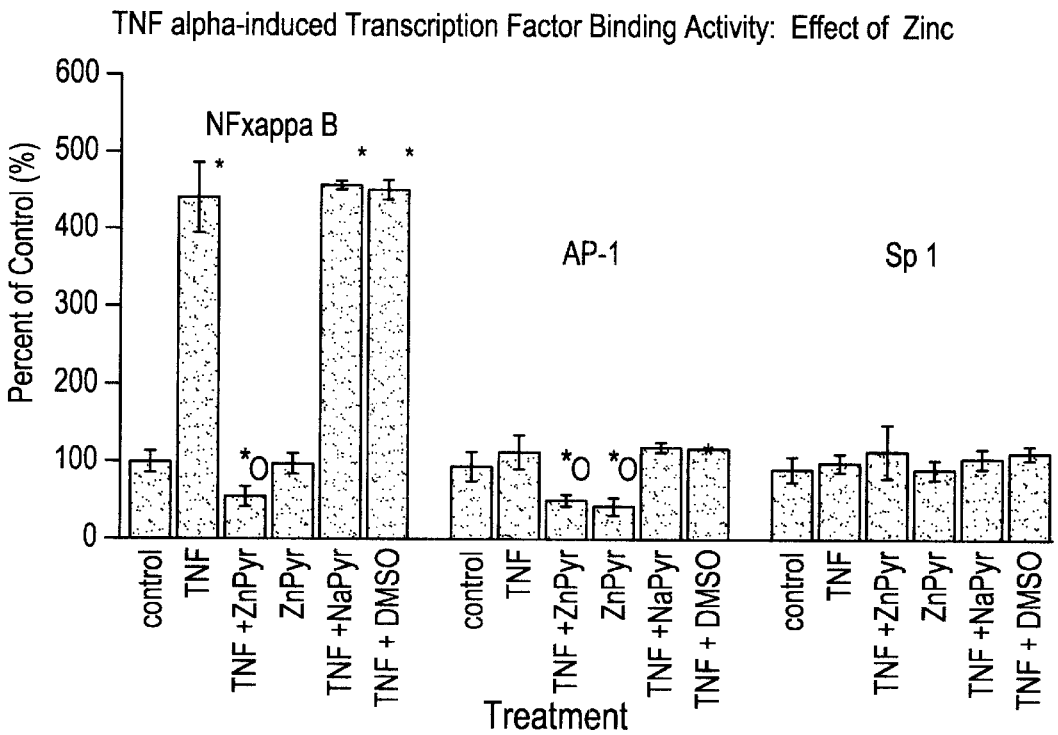
FIG. 14 shows the effects of zinc pyrithione on the TNFα-induced transcription factor binding activity in human primary endothelial cells.
Figure 15:
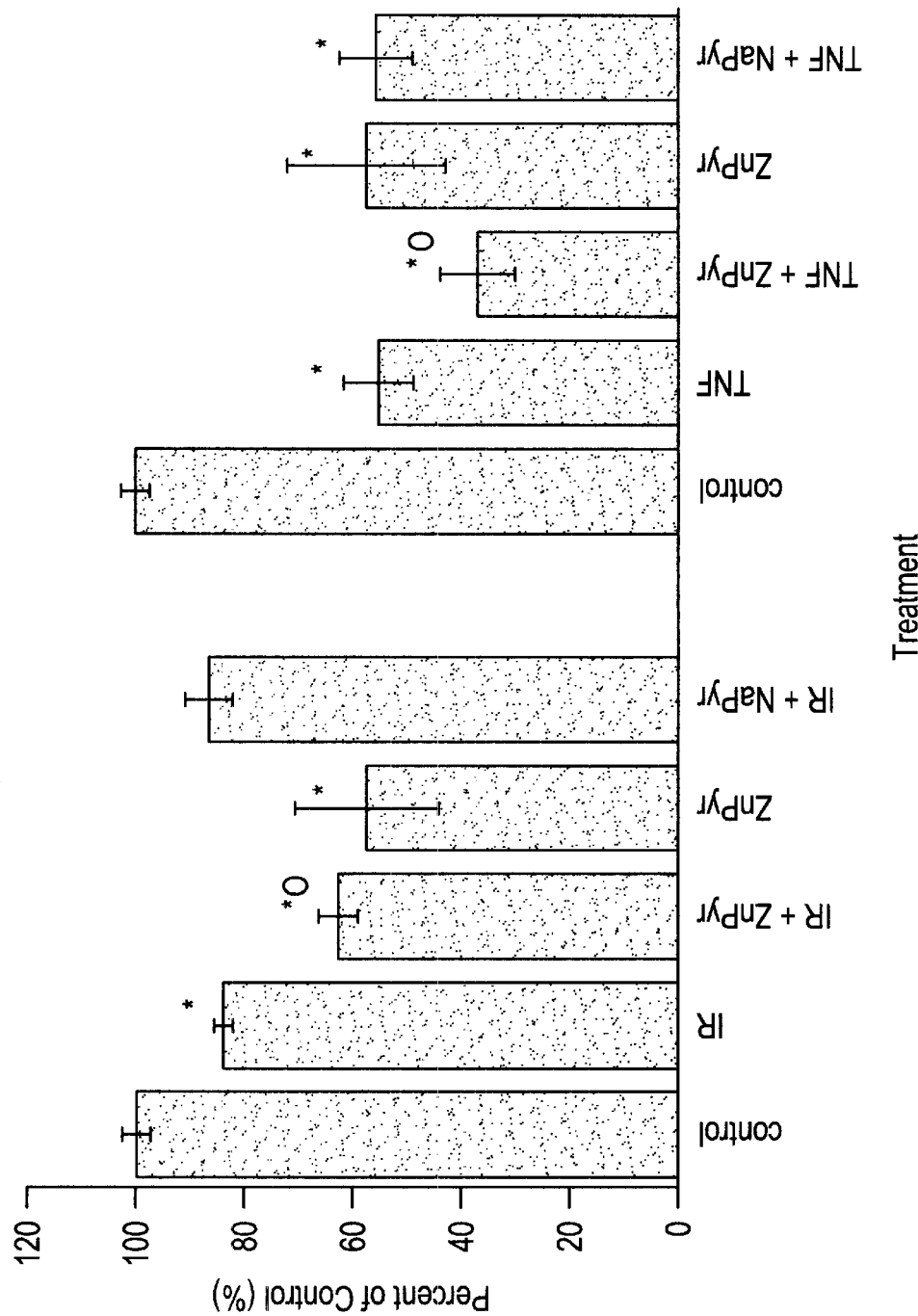
FIG. 15 shows the effects of zinc pyrithione on cytosolic Ikappa B protein levels in human primary endothelial cells.

EMSA tests showed that irradiation-induced apoptosis is associated with a significant increase in nuclear NF-kB content, and that zinc-pyrithione, but not sodium-pyrithione or DMSO alone, blocked this increase (FIG. 13). Zinc-pyrithione also lowered the nuclear content of AP-1, but did not appear to affect Sp1 in this model. (*, $P<0.05$ vs. Control; °, $P<0.05$ vs. irradiated group, n=4). Zinc-pyrithione had a very similar effect in TNFα-treated HUVEC (FIG. 14, and was particularly potent at blocking the TNFα-induced increase in NF-kB content. (*, °, same as above, n=3). Since NF-kB is associated with the cytosolic inhibitor IkB which governs its activity in the cell, the effect of zinc-pyrithione on the cytosolic level of this protein was examined. The data show that zinc-pyrithione lowered the cytosolic content of IkB in cells treated with either radiation or TNFα (FIG. 15).

EXAMPLE 6

Effects of Zinc Pyrithione on Models of Ischemic Stroke in Rodents

Stroke is an extremely variable clinical condition which reflects the variability of the underlying disease process. The vascular occlusion can occur at many different sites in the brain and the cause of the occlusion, the severity of the problem, and the degree of reversibility can all contribute to the variability of outcome. In contrast, in experimental animal models most of these variables can be controlled or eliminated, enabling a meaningful interpretation of the results. Generally, stroke models are grouped into those producing either global or focal ischemia (Ginsberg, M. D. & Busto, R. (1989) Stroke, 20:1627–1642, incoporated herein by reference; Ginsberg, M. D. & Busto, R. (1998) Small-Animal Models of global and focal cerebral ischemia. In Cerebrovascular Disease: Pathophysiology, Diagnosis, and Management (ed. Malden, M. A.), pp. 14–35, Blackwell Science, incoporated herein by reference). It is generally understood that global models are more relevant to cardiac arrest, while focal models are of greater relevance to acute ischemic stroke.

To study the possible neuroprotective effects of zinc pyrithione (ZP) two models of stroke were used: a global ischemia-reperfusion model of 4 vessel occlusion in rats (4VO) and a focal ischemia model of middle cerebral artery occlusion in mice (MCAO). The 4VO approach sealed off the two carotid and two vertebral arteries which carry all the blood to the brain. This approach permitted severe forebrain ischemia to be produced in awake and freely moving rats, and produced reproducible neuropathology. The 4VO is a two-stage operative procedure (Pulsinelli, et al., (1979) Stroke, 10: 267–272, incorporated herein by reference). In the first stage, the vertebral arteries were exposed and permanently sealed by electrocauterization (Pulsinelli, et al., (1988) Stroke, 19:913–914, incorporated herein by reference). This occlusion of the vertebral arteries does not in itself cause serious injury in the rat. It is the second stage which initiated the injurious ischemic episode. It was performed 24 h later and involved the brief occlusion of the carotid arteries, shutting off all blood flow to the brain. Although there was a marked mortality during both stages even in laboratories which are highly experienced in this procedure (Ginsberg, et al., (1989) supra) the 4VO is a favorite stroke model because it results in highly reproducible damage in the CA1 region of the hippocampus, as well as in some other brain regions.

MCAO in mice is one of the most clinically relevant stroke models. It shuts off blood flow to only a portion of the brain, producing a focal injury which closely resembles the clinical situation with stroke patients. This procedure was performed with an intraluminal thread. A nylon suture was introduced into the external carotid artery and was gently advanced into the internal carotid artery. The diameter of the suture was such that it lodged in the anterior cerebral artery, occluding the medial cerebral artery at its origin. Brain damage in this model was observed as early as several hours after the ischemic episode, with optimal injury occurring at 24 h. The injury occupied a large part of the hemisphere including the cerebral cortex and subcortical structures, and its severity depended on the duration of ischemia and the strain of mice used.

Animals

The 4VO procedure was performed on male Wistar rats weighing 240–300 g. The rats were housed in groups of 5 in plastic cages with free access to food and water. The MCAO protocol was performed on male C57BL/6 mice weighing 20–28 g which were housed in groups of 10 in plastic cages with free access to food and water. All experiments were performed in accordance with the National Institutes of Health Guidelines for the Care and Use of Laboratory Animals.

Surgeries
4VO in Rats

Rats under chloral hydrate anesthesia (325 mg/kg) were positioned in a stereotaxic frame. The vertebral arteries were exposed and permanently occluded by electrocautery at the first cervical vertebra. Snares (surgical silk strings) were then placed loosely around each common carotid artery without interrupting the carotid blood flow. The animals were then allowed to recover for 24 hours with free access to water. On the following day, the rats were lightly anesthetized with ether, were secured to surgical boards, ventral side up, and their common carotid arteries were exposed. Forebrain ischemia was initiated by tightening the snares around the carotid arteries for 10 min. The body temperature of the rats was carefully maintained at ~37–37.5° C., both before and during the ischemic insult, using a feedback-controlled heating pad and a rectal thermistor (Homeothermic Blanket System, Harvard Apparatus LTD, England). The initial ($1^{st}$ min of ischemia) and final ($10^{th}$ minute of ischemia) temperature did not differ among all groups of rats studied. After the ischemic episode, the temperature was maintained in similar fashion at 37° C. for at least 4 h. Only rats that showed signs of severe neurological injury, such as a loss of the righting reflex, pupil dilation, etc., were included in this study. In the sham-operated controls, the vertebral and carotid arteries were exposed, but were not occluded. Evaluations of neurological deficit were performed at 24 and 96 h after ischemia, and were based on a scoring system which recorded activity level, motility, pain reflex, grabbing reflex, and the ability to see and hear (Miljkovic, L. M., et al., (1997) Ann. Emerg. Med. 29, 758–765, incorporated herein by reference).

MCAO in Mice

Mice (C57BL/6) were anesthetized with an intraperitoneal injection of chloral hydrate (350 mg/kg) and xylasine (4 mg/kg). Focal cerebral ischemia was produced by occlusion of the MCA using the intraluminal filament technique (Longa, Z. E., et al., (1989) Stroke 20:84–91,incorporated herein by reference). A 8.0 nylon microfilament coated with a silicon resin (Xantopren)—hardener mixture (Hara, H., et al., (1996) J. Cereb. Blood Flow Metab. 16:605–611, incorporated herein by reference) was inserted into the left common carotid artery, and was advanced 10–11 mm distal to the carotid bifurcation so as to occlude the MCA and posterior communicating artery. The filament was left in this position for 1 h. For reperfusion, the animals were re-anesthetized briefly and the filament was withdrawn to restore the blood flow. Core temperature was maintained at ~37° C. with a homeothermic blanket for a period of 2 h following reperfusion. The neurological deficit caused by the ischemic insult was scored after 2 h of reperfusion according to the scheme of Bederson, J. B., et al. (1986) Stroke 17:472–476, incorporated herein by reference: 0, no observable neurological deficit (normal); 1, failure to extend the right forepaw (mild); 2, circling to the contralateral side (moderate); 3, falling to the right (severe); 4, inability to walk spontaneously (most severe).

Zinc Ionophore Treatments

The zinc pyrithione (ZP) data presented were derived with a treatment protocol in which ZP was injected in three boluses, at 10 min, 1 h, and 2 h after the termination of the ischemic episode, through a tail vein catheter. With the 4VO rat model, four doses of ZP: 3×1.2 µg/kg, 3×6 µg/kg, 3×30 µg/kg, and 3×200 µg/kg were tested. With the mouse MCAO model only the three lowest concentrations of ZP were tested. Some data were also obtained with a second ZP treatment protocol in which three boluses of 6 µg/kg (3×6 µg/kg) were injected at 3, 4, and 6 h after the termination of the ischemic episode. In addition, a treatment protocol with zinc-diethyldithiocarbamate (ZnDDC) was performed with both the 4VO and MCAO models using the dose of 3×7.6 µg/kg, a regimen which delivers zinc at a dose equivalent to that delivered with 3×6 µg/kg of zinc pyrithione.

The zinc ionophore solutions were prepared by diluting a stock solution of ZP and ZnDDC in DMSO with saline. The final concentration of DMSO in the injectate was 2.5%. Control animals receiving vehicle-alone were injected with 2.5% DMSO in saline.

Histology
4VO

Four days post surgery, control and experimental animals were deeply anaesthetized with sodium thiopental (60 mg/kg, intraperitoneally) and were perfused transcardially with 250 ml of AFA fixative (96% alcohol, 39% formalin, glacial acetic acid, 7:2:1). After the AFA perfusion the heads were collected intact and were kept at 4° C. for 4–5 h. The brains were then removed and immersed in the same fixative for 1 h, and were then stored in 70% alcohol. Each forebrain was cut into three frontal blocks and imbedded in paraffin. Ten um thick sections were cut from a region 3.0–4.0 mm posterior to the bregma. The sections were stained with cresyl violet (Nissl). Computer images of the stained sections were prepared, and the total number of viable pyramidal neurons was counted in a 500 µm-long section of the CA1 region in the hippocampus. The person doing the cell counts was blinded as to the identity of the experimental groups. In Situ End Labeling (ISEL), a protocol for identifying apoptotic cells by staining fragmented DNA, was performed according to a protocol developed in the laboratory of Dr. Fliss (Schmidt-Kastner, et al., (1997) Stroke 28: 163–170, incorporated herein by reference) using deparaffinized 10 µm thick brain sections from rats sacrificed at 24 h and 96 h after ischemia. Fluorescence was monitored with a Zeiss Axioplan microscope.

MCAO

Mice were killed 24 h after reperfusion with an overdose of sodium thiopental (60 mg/kg, intraperitoneally), and the brain was rapidly removed and sectioned coronally into five 1.7 mm slices. The slices were then placed in 2% (wt/vol) 2,3,5-triphenyltetrazolium chloride solution (TTC) in PBS (pH 7.4) for 20 min at 37° C. This procedure, which tests mitochondrial activity, stains viable tissue a bright red, while the infarcted regions remain white. Following TTC staining the sections were fixed in 10% formalin overnight. The area of infarct in each section was determined using an image-analysis system. The infarct volume was subsequently calculated by summing the infarct areas in the sequential 1.7 mm-thick sections with correction for edema. The person measuring infarct volumes was blinded as to the identity of the experimental groups. For ISEL staining, the brains were removed, were frozen rapidly, and were sectioned with a cryostat into 20 µm sections from the anterior side to the posterior side at 500 µm intervals. ISEL was performed as described above. Adjacent sections were stained with cresyl violet (Nissl). The ApopTag® Peroxidase In situ Apoptosis detection Kit (Intergen) was also used to detect apoptosis in mouse brain sections.

Statistics

The data were expressed as means ±S.E.M. One way-ANOVA with post hoc Duncan's test or T-test for independent samples were used for statistical analysis of data.

Zinc Ionophore Toxicity

No noticeable changes in behavior or appearance were detected in animals injected with lower doses of ZP, or the single dose of ZnDDC, when compared to those receiving vehicle alone. The weight loss in rats after 4VO (7.5–16.9% at 24 h after ischemia and 4.1–11.2% at 96 h after ischemia) did not differ between the vehicle-treated and ZP-treated groups.

4VO model (10 min-1 h–2 h-Injection Schedule)

Neuronal Cell Loss

Figure 16A:
FIGS. 16A–16C show photomicrographs depicting histological evidence of protection by zinc-pyrithione in 4 vessel occlusion stroke model in rats.
Figure 16B:
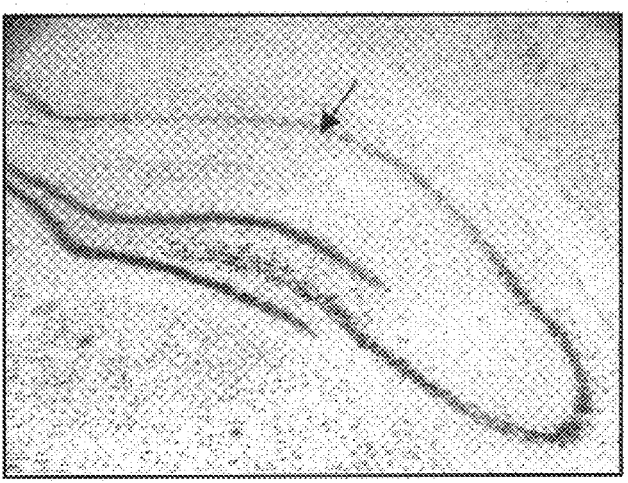
Figure 16C:
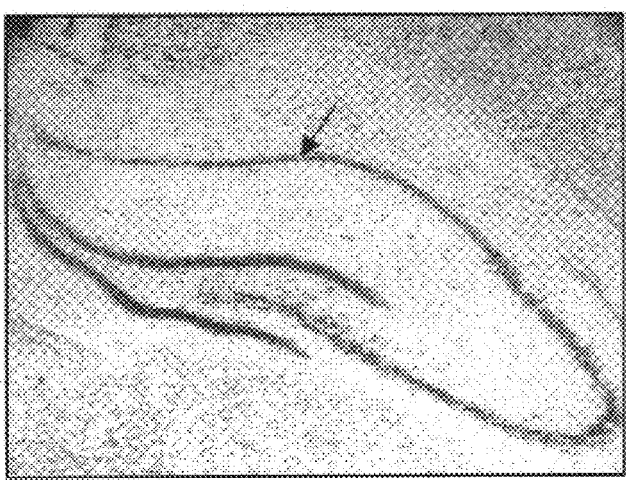
Figure 17A:
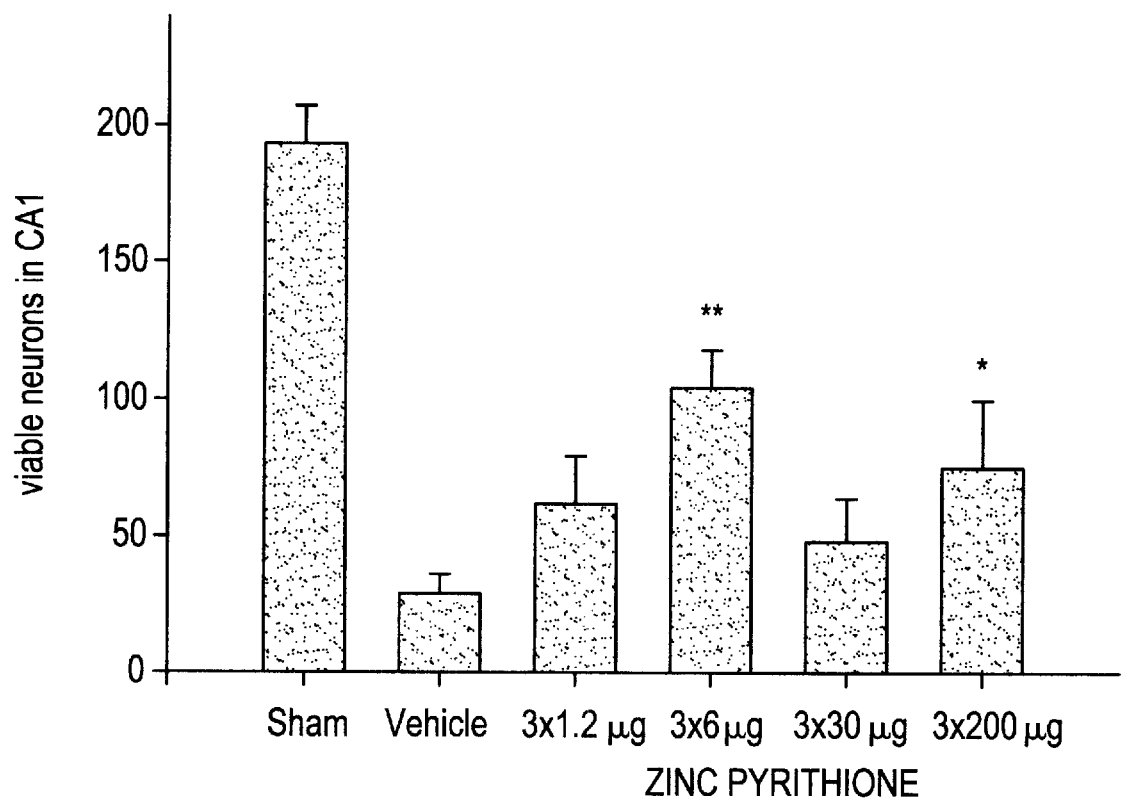
FIG. 17A shows the effect of zinc pyrithione on neuronal survival in 4 vessel occlusion stroke model in rats.

Approximately 15% of the neurons in the CA1 region survived the ischemic insult in the vehicle-treated group when compared to the sham-operated animals. However, treatment with ZP showed pronounced protection and increased the number of viable cells (FIG. 16). The ZP-mediated increase in cell survival varied (1.6–3.5 fold) and did not show a clear dose-dependence (FIG. 17A). Although all doses of ZP tested showed evidence of protection, the 3×6 µg/kg group reached statistical significance with approximately 52% of the pyramidal cells surviving the ischemic episode. One-way ANOVA (sham, vehicle, and ZP-treated groups) showed a significant dependence of the viable cell number in the CA1 on the experimental treatment conditions (F=12.9, P<0.000001). The post hoc Duncan's test showed the difference of all ZP and vehicle-treated groups from shams at P<0.01, with the ZP 3×6 µg/kg group significantly different from vehicle at P<0.01, and the 3×200 µg/kg ZP group showing a trend at P<0.09. Thus, 3×6 µg/kg appeared to be the optimal protective dose of ZP in this model. However, the trend for significant protection shown by the 3×200 µg/kg ZP group, and the collective evidence of protection at the other doses suggested that ZP is protective over a broad range of doses.

Figure 17B:
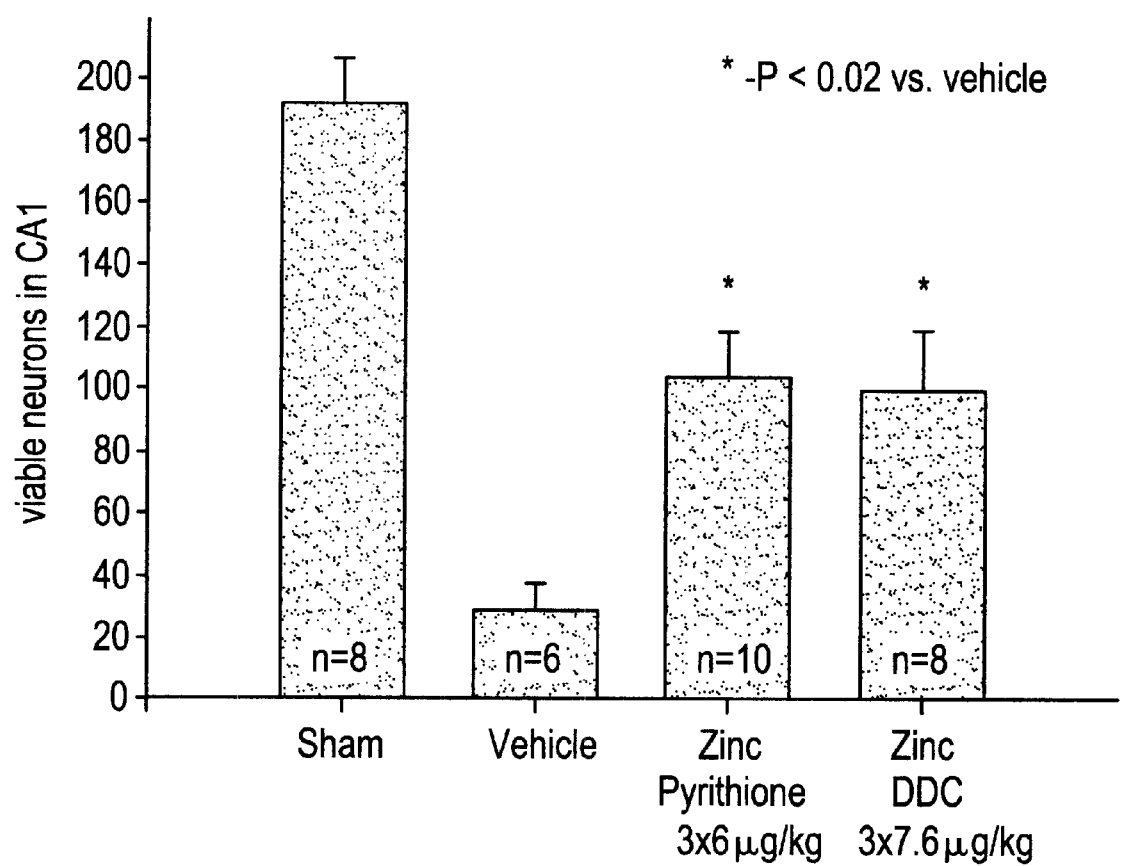
FIG. 17B shows the effect of zinc-pyrithione, zinc-diethyldithiocarbamate on neuronal survival in 4 vessel occlusion stroke model in rats.

In addition, with ZnDDC at 3×7.6 µg/kg, the number of viable neurons in the CA1 region was 99.5±19.9, showing that the protection with this dose of ZnDDC was similar to that achieved with 3×6 µg/kg of ZP, a dose which delivered the same amount of zinc (FIG. 17B).

ISEL Staining

As described above, ZP at 3×6 µg/kg showed significant protection against neuronal cell death. However, the data do not indicate if this cell death was apoptotic or necrotic in nature. To determine if the ZP-dependent increase in cell survival was attributable to a lower incidence of apoptosis we performed ISEL on brain sections.

Figure 18:
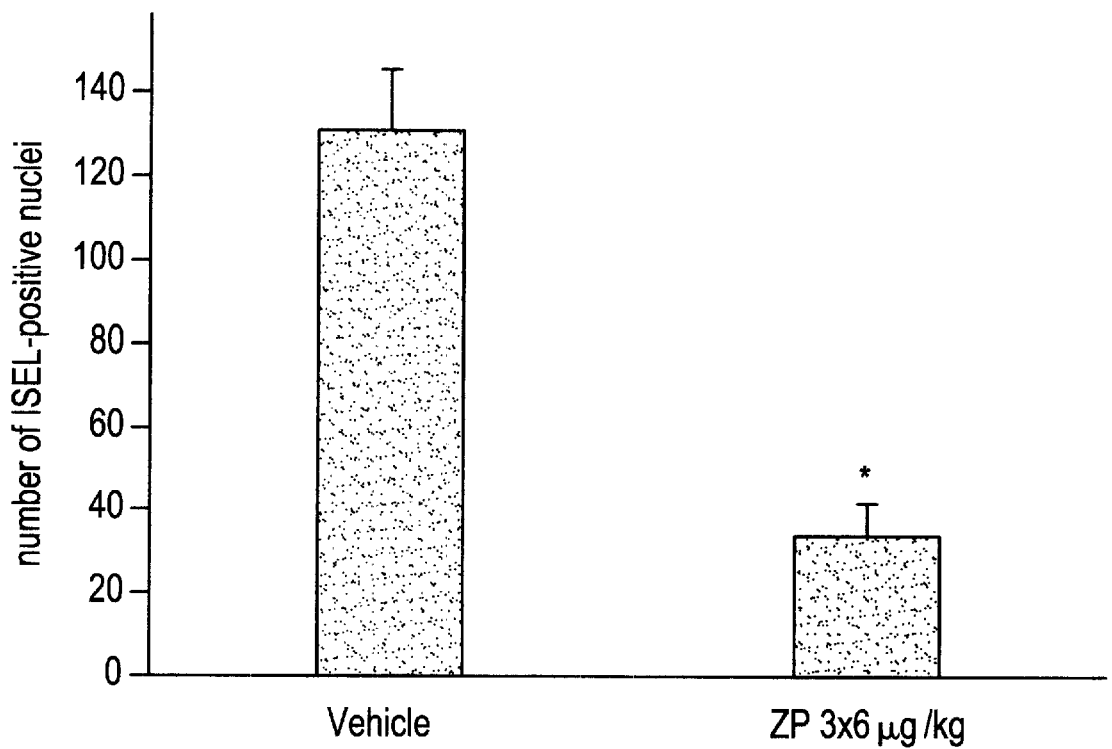
FIG. 18 shows the effect of zinc pyrithione in rats and a 4× reduction in the number of apoptotic nuclei in a 4 vessel occlusion stroke model in rats.

At 24 h after ischemia no apoptotic cells were observed in the sham, vehicle-treated, or ZP (3×6 µg/kg)-treated groups (n=5 for each group), suggesting that apoptosis required a longer post-ischemic period to manifest itself in this model. Apoptosis was more commonly observed at 96 h after ischemia. Numerous ISEL-positive nuclei were observed in the hippocampi of vehicle-treated rats (131.4±14.6 in CA1 region, n=5). However, in rats treated with 3×6 µg/kg ZP, the number of apoptotic nuclei was approximately 4 times lower (33.6±7.8, n=9, P<0.0001, t-test) (FIG. 18). No apoptosis was detected in any brain region of the sham-operated rats. The data therefore indicated that ZP has a potent anti-apoptotic effect in this model, and that it is this effect which accounted for the observed neuronal protection.

Neurological Deficit

The neurological deficit data in 4VO rats are presented in Table 3. A method of scoring in which increasing neurological scores are indicative of decreasing neurological function compared to a perfect score of 0 for the shams was employed. For example, a large number of the 4VO rats did not show any neurological deficit (score 0), despite the fact that they sustained an almost complete loss of cells in the CA1 region. Therefore, the administration of ZP did not influence the neurological deficit in the 4VO rats despite clear evidence of histological protection.

4VO Model (3 h, 4 h, 6 h Injection Schedule)

Administration of ZP in boluses of 6 µg/kg at 3, 4, and 6 h after the ischemic episode (3×6 µg/kg) significantly increased neuronal viability in the CA1 region, with the number of viable neurons increasing 2.5 fold vs. the vehicle-treated group. The cell count was 73.2±15.0 in the ZP-treated group vs. 29.2±7.8 in the vehicle-treated group (P<0.03, t-test). The viable cell counts in the 3×6 µg/kg groups of both injection regimens (10 min, 1 h, 2 h or 3, 4, and 6 h after ischemic episode) did not differ significantly (103.5±15.2 vs. 73.2±15.0). The neurological deficit data for this ZP administration schedule are presented in Table 3. The neurological score in "3, 4, 6 h schedule" rats did not differ from that in the other regimen (10 min, 1 h, 2 h after ischemic episode). These data therefore indicated that delaying the first administration of ZP by 3 hours did not significantly change its neuroprotective effect at the dose of 3×6 µg/kg, indicating a possible wide therapeutic window for ZP in the 4VO stroke model.

MCAO

Figure 19:
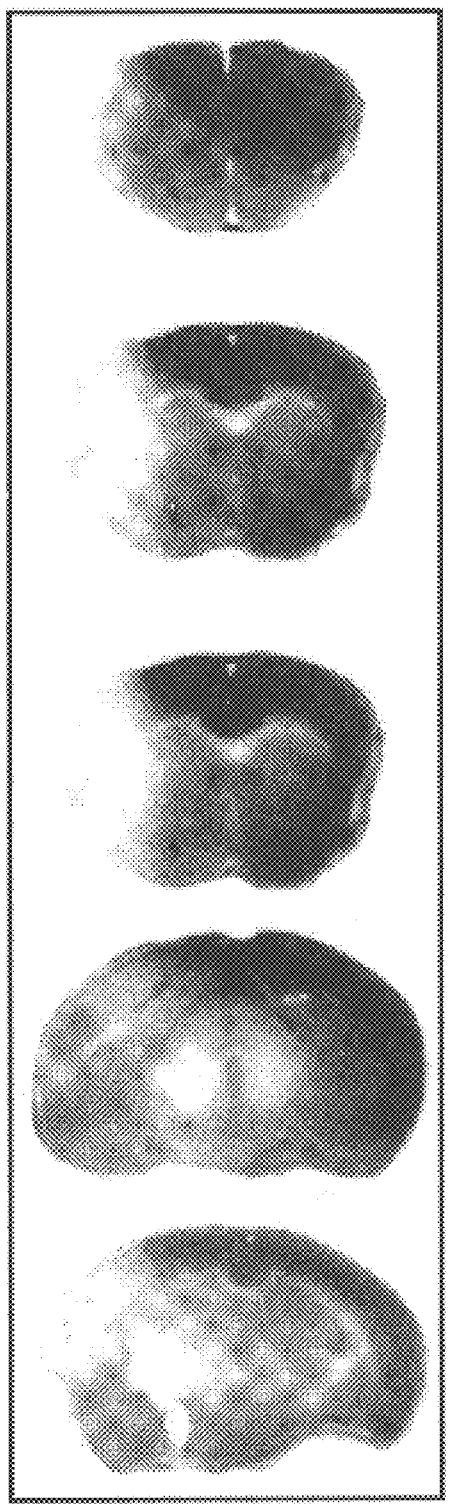
FIG. 19 shows middle cerebral artery occlusion caused infarcts in the left hemisphere of mouse brain. Infarcts are visible as white regions in the left hemisphere.
Figure 20A:
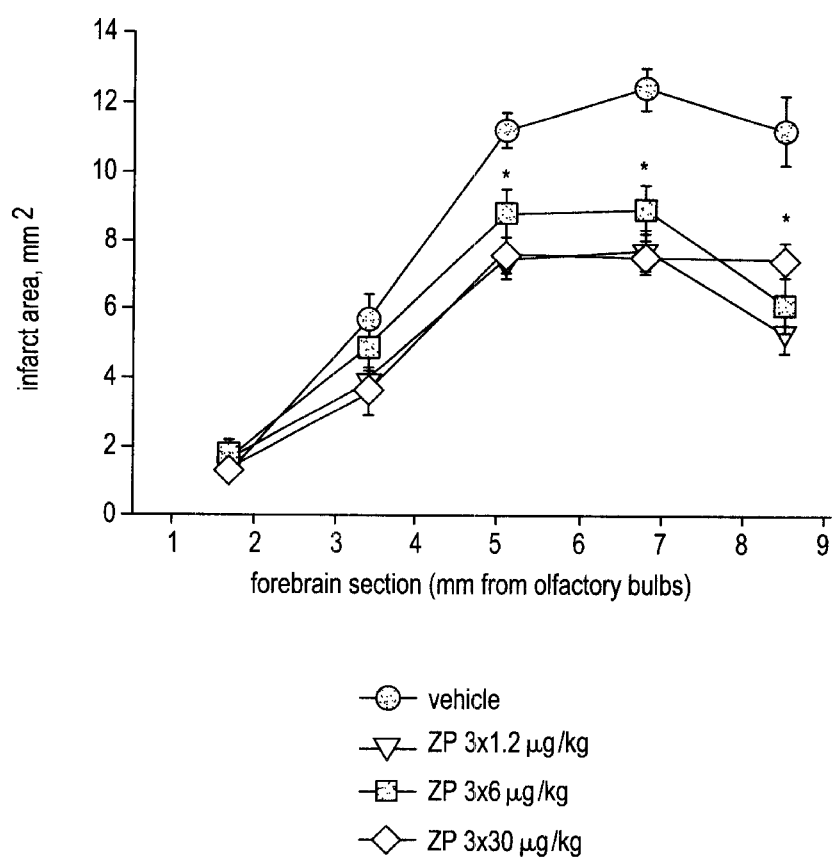
FIG. 20A shows the reduction in infarct area upon treatment with zinc-pyrithione in mice with middle cerebral artery occlusion stroke model.
Figure 20B:
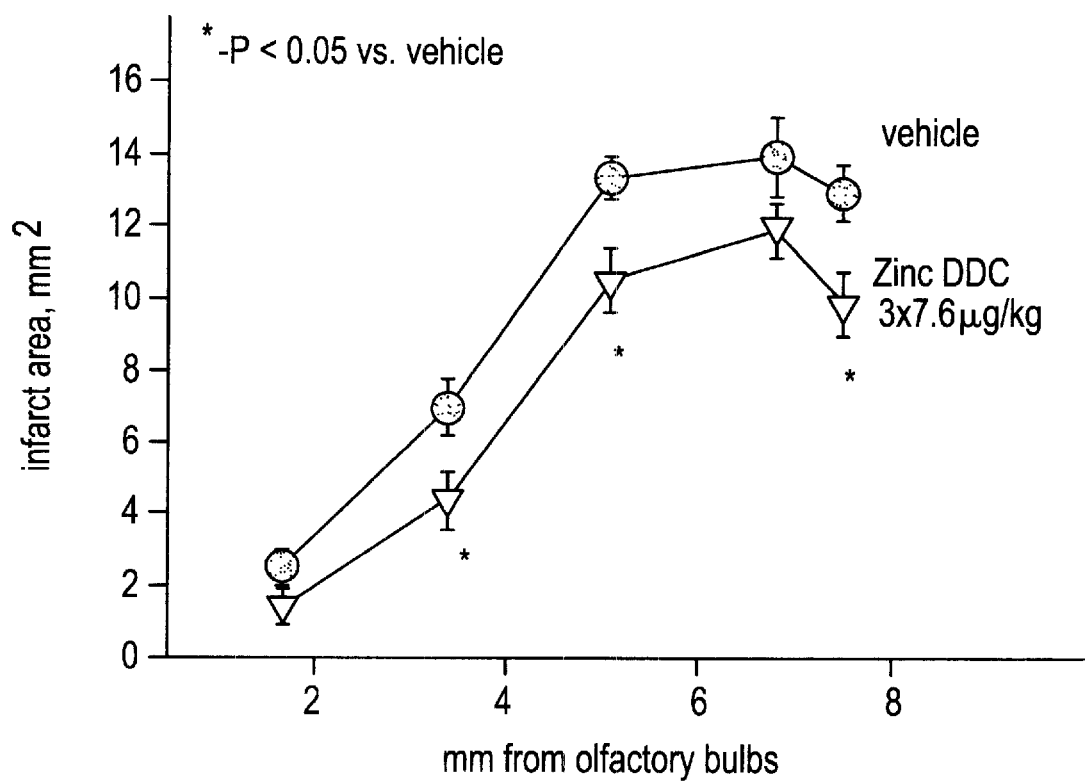
FIG. 20B shows the reduction in infarct area upon treatment with zinc-diethyldithiocarbamate in mice with middle cerebral artery occlusion stroke model.

MCAO for 1 h produced significant infarcts in the left hemisphere of mouse brain (FIG. 19). Three doses of ZP were used (3×1.2 µg/kg, 3×6 µg/kg, and 3×30 µg/kg) and infarct areas, infarct volumes and neurological scores were measured. ZP at all three doses significantly decreased the infarct area at a distance of 3.4–5.8 mm from the frontal pole (FIG. 20A). One-way ANOVA (vehicle and ZP-treated groups) showed a dependence of infarct size in sections 3, 4, and 5 (3.4, 4.1, and 5.8 mm from the frontal pole) on the experimental treatments with F=7.8 (P=0.0003), 13.0 (P=0.000003), and 11.7 (P=0.00001), respectively. The post hoc Duncan's test showed a significant difference between infarct size and vehicle at P<0.01 in sections 3–5 for each ZP dose. The infarct size did not differ significantly between the ZP groups. In addition, ZnDDC at 3×7.6 µg/kg also significantly decreased the infarct area in this model (FIG. 20B).

Table 4 presents data on the absolute and relative (% of the contralateral hemisphere) infarct volumes in the mouse MCAO model in response to zinc pyrithione treatment. The calculated infarct volumes in the ischemic control mice were similar to those reported previously for this strain of mouse (Hara, H., et al. (1996) J. Cereb. Blood Flow Metab. 16:605–611; MacManus, J. P., et al., (1999) NeuroReport 10:2711–2714; Nagayama, M., et al., (1999) J Cereb. Blood Flow Metab. 11:1213–1219; Nogawa, S., et al., (1998) Proc. Natl. Acad. Sci. USA. 95: 10966–10971; Takagi, Y., et al., (1999) Proc. Natl. Acad. Sci. USA. 96:4131–4136). Vehicle alone (2.5% DMSO) produced apparently contradictory effects. It tended to increase the infarct volume but concomitantly decreased the neurological score. However, these effects were not statistically significant.

Figure 21B:
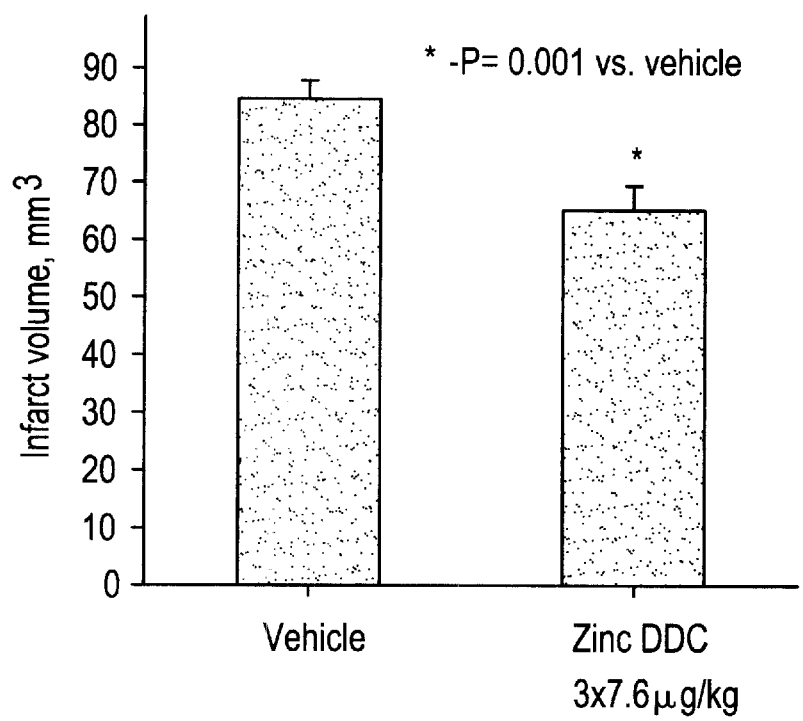
FIGS. 21B and 21C show the administration of zinc-diethyldithiocarbamate decreased infarct volumes in mouse brain.
Figure 21C:
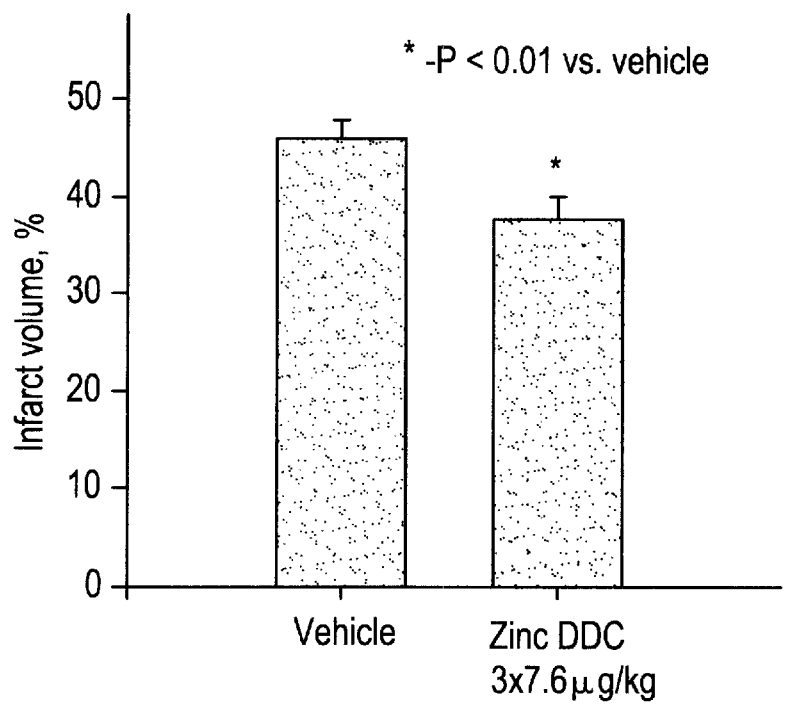

The administration of ZP at all three doses statistically significantly decreased both the absolute (data not shown) and relative infarct volumes by 29.0–38.2% and 30.8–40.0%, depending on the dose, respectively) compared with the vehicle-treated group (FIG. 21A). Comparison of control, vehicle-, and ZP-treated groups using one-way ANOVA showed a significant dependence of both absolute and relative infarct volumes on the experimental treatments (F=10.1, P<0.00005; F=8.2, P<0.00005, respectively). Highly significant differences (Duncan's test) between the control and each of the ZP groups (p<0.05), as well as between the vehicle and the ZP groups (P<0.001) was shown for both the absolute and relative infarct values. In addition, ZnDDC at 3×7.6 µg/kg also significantly decreased both the absolute and relative infarct volumes in this model (FIGS. 21B and 21C).

Figure 22:
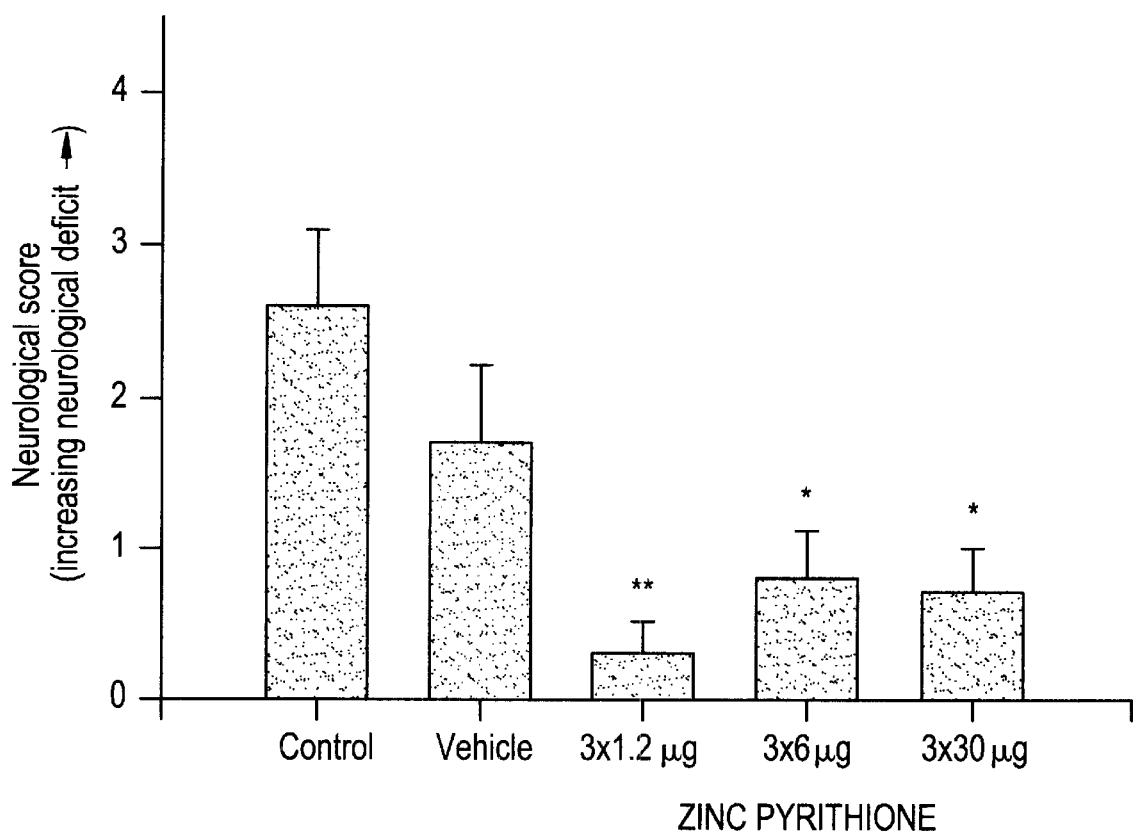
FIG. 22 shows the effect of zinc-pyrithione administration on a neurological score in mice with middle cerebral artery occlusion stroke model.

Clear evidence of protection by ZP was also observed with the neurological score (FIG. 22). In the vehicle treated groups 4 out of the 10 mice (40%) showed no apparent neurological deficits (zero neurological score) even though they had significant infarctions. Such animals were not common in the control group (12.5%). In contrast, in the ZP-treated groups the number of mice developing infarct but having no neurological deficit increased to 84.6% in the 3×1.2 µg/kg group, 61.5% in the 3×6 µg/kg group, and 63.6% in the 3×30 µg/kg group.

Moreover, no severe deficits (neurological score of 3 or 4) were observed in the ZP-treated groups (the only exception was one mouse with the score of 3 in the 3×30 µg/kg group). One-way ANOVA showed a statistically significant dependence of neurological score on ZP (F=2.9, P<0.05). The difference between the vehicle and the 3×1.2 µg/kg group was significant (P<0.01, post hoc Duncan's test), while the difference between the vehicle and the two other ZP doses tended to be significant (P<0.06, trend).

TABLE 3

Neurological deficit in 4VO rats (neurological score, mean ± S.E.M.)

| Group | N | 24 h | 96 h |
|---|---|---|---|
| Vehicle | 8 | 2.1 ± 1.0 | 1.4 ± 0.9 |
| ZP 3 × 1.2 µg/kg | 9 | 2.1 ± 0.9 | 0.4 ± 0.2 |
| ZP 3 × 6 µg/kg | 10 | 1.4 ± 0.4 | 1.4 ± 0.6 |
| ZP 3 × 30 µg/kg | 5 | 2.8 ± 1.0 | 1.6 ± 0.7 |
| ZP 3 × 200 µg/kg | 5 | 2.4 ± 1.3 | 2.0 ± 1.1 |
| ZP 3 × 6 µg/kg * | 6 | 1.3 ± 0.7 | 0.8 ± 0.4 |

* ZP administered 3, 4, and 6 h after the ischemic episode.

TABLE 4

Infarct volumes and neurological deficit in mice following 60 min MCAO (mean ± S.E.M.)

| Group | N | Infarct volume, mm$^3$ | Infarct volume, % of contralateral hemisphere | Neurological deficit |
|---|---|---|---|---|
| Control (no injections) | 9 | 61.2 ± 3.6 | 33.6 ± 2.5 | 2.6 ± 0.5 |
| Vehicle-treated | 10 | 71.3 ± 3.9 | 41.5 ± 4.6 | 1.7 ± 0.5 |
| ZP 3 × 1.2 µg/kg | 13 | 44.0 ± 2.6***# | 24.9 ± 1.5***# | 0.3 ± 0.2**# |
| ZP 3 × 6 µg/kg | 13 | 50.6 ± 4.7*** | 28.7 ± 2.5*** | 0.8 ± 0.3*## |
| ZP 3 × 30 µg/kg | 11 | 45.5 ± 1.5***# | 24.9 ± 0.8***# | 0.7 ± 0.3*## |

*P < 0.06 vs. vehicle-treated group;
**P < 0.01 vs. vehicle-treated group;
***P < 0.001 vs. vehicle-treated group.
P < 0.05 vs. control group;
P < 0.01 vs. control group

EXAMPLE 7

In Vivo Heart Model—Ischemic Injury in Pigs.
Experimental Model:

Adult pigs of either sex weighing 20–30 kg will be used for this study. The pigs will be premedicated with an intramuscular injection of Ketamine at a dose of 11 mg/kg, and Midazolam at a dose of 0.2 mg/kg, 30 min prior to induction of anesthesia. Anesthesia will be initiated with Isoflurane with oxygen to a surgical plane before the animals will be intubated with an endotracheal tube. Anesthesia will be maintained with Isoflurane (generally 2%) and oxygen (1–2 L/min). Assisted ventilation (10–15 ml/kg tidal volume; rate 20–40 breathes per minute) will be used for the surgical procedure. Fluid will be administered through an ear vein using saline 0.9% at a rate of 10 ml/kg/hour. The rate will be increased accordingly in the presence of hemorrhage. Temperature will be maintained with a circulating warm water blanket. Central venous and arterial lines will be introduced in the carotid artery and the internal jugular veins for a Swan Ganz sheath and a catheter for drug administration. Local anesthesia will be provided by means of epidural injection of morphine (1 mg) diluted in 5 ml 0.9% NaCl. Local nerve blocks will also be achieved by infiltrating Marcaine along the proximal and lateral borders of the sternum. Local blocks will be repeated every 4 hours. A Lidocaine drip will be administered via one of the jugular catheters at a rate of 20–40 ml/hr. A midline sternotomy will be performed. A lidocaine bolus at 1–2 mg/kg will be administered before any manipulation of the heart. The pericardium will be opened and fixed to the border of the sternum to form a pericardial cradle. A snare will be applied by tunneling the LAD with a monofil suture approximately half way down the vessel. Coronary occlusion will be achieved by tightening the snare around the LAD for 45 min. The snare will then be loosened to 5 initiate reperfusion.

ECG, central venous pressure, pulmonary artery, and arterial pressure will be monitored continuously on a Siemens Sirecust 404–1. Cardiac output will be determined by thermodilution (5 ml NaCl 0.9%, room temperature). Arteriovenous $O_2$ differences will be determined before, 20, and 45 minutes after coronary occlusion, and after 10 and 120 minutes of reperfusion. Blood gas analysis will be performed with the Radiometer Copenhagen ABL 77. Venous blood samples (3 ml) will be collected in polypropylene tubes containing citrate and will be centrifuged at 2000 g for 15 minutes at 4° C. Plasma creatine kinase activity will be determined and expressed as international units per milliliter. Troponin-T will be measured.

Two models will be tested: I. An acute non-survival model with a total of 4 h reperfusion, and II. A recovery model with 7 days of reperfusion. Each of the two models will consist of 5 groups: 1) Sham operated, 2) Ischemia/reperfusion alone, 3) I/R plus vehicle alone, 4) I/R plus zinc pyrithione, and 5) I/R plus Zinc-diethyldithiocarbamate. The zinc ionophores, or vehicle, will be infused into the jugular vein at a dose of 8.3 ng/kg body weight at 0, 1, and 2 h after the initiation of reperfusion in a total of 30 ml of saline in a blinded fashion under maintenance of constant flow and pressure. Hemodynamic and $PO_2$ measurements, as well as blood samples will be obtained before; 5, 10, 30, and 45 minutes after coronary occlusion; and after 5, 10, 30, 60, 120, and 240 minutes of coronary reperfusion. At the end of reperfusion, the pigs will be sacrificed with 2M KCl (1 ml/kg), and their hearts will be recovered for further analysis.

With model I (non-survival), after 4 h of reperfusion, the left anterior descending coronary artery (LAD) will be reoccluded. Then, 60 ml of Evan's blue (2% wt/vol solution) will be injected into the left atrium to stain perfused myocardium. Unstained myocardium will be defined as the area at risk. After injection of 2M KCl, the heart will be excised. The right ventricle, the large vessels, and fat tissue will be removed. The left ventricle will then be sliced perpendicular to the axis of the left side of the heart from the apex to the AV groove in 6–7 mm slices. The unstained part of the left ventricular myocardium will be separated from the Evan's blue-stained portion and immersed in a 0.09-mol/L sodium phosphate buffer, pH 7.4, containing 1% triphenyltetrazolium chloride (TTC, Sigma) and 8% dextran (molecular weight, 77.800) for 20 minutes at 37° C. The TTC dye will form a dark-red formazan complex in the presence of viable myocardial cells that contain active dehydrogenases and cofactors. Dead cells will remain unstained. The ischemic but non-necrotic, red-stained tissue will be separated from the unstained, infarcted tissue. The three tissue sections-nonischemic (area not at risk), ischemic non-necrotic, and ischemic necrotic tissue will be weighed. TUNEL staining, as described above (Fliss, et al. (1996), incorporated herein by reference), will be used to identify the percent of apoptotic myocytes in the myocardial tissue.

What is claimed is:

1. A method of treating seizures comprising administering to a subject in need of thereof an effective amount of a zinc ionophore and a pharmaceutically acceptable carrier.

2. The method of claim 1, wherein the zinc ionophore comprises of zinc pyrithone, heterocyclic amines, dithiocarbamates and Vitamins.

3. The method of claim 2, wherein the zinc ionophore is zinc pyrithione.

4. The method of claim 2, wherein said heterocyclic amine comprises 5,7-Diiode-8-hydroxyquinoline and 8-Hydroxyquinoline.

5. The method of claim 2, wherein said dithiocarbamate comprises pyrrolidine dithiocarbamate, zinc-diethyldithiocarbamate, disulfiram and zinc-dimethyldithiocarbamate.

6. The method of claim 2, wherein said vitamin is selected from the group consisting of Vitamin E and Vitamin A.

7. The method of claim 1, wherein the effective amount of a zinc ionophore ranges from about 0.005 µg per kg of body weight to about 5.0 mg per kg of body weight.

8. The method of claim 7, wherein the effective amount of a zinc ionophore ranges from about 0.2 µg per kg of body weight to about 600 µg per kg of body weight.

9. A method of treating conditions caused by apoptosis comprising administering to a subject in need thereof an effective amount of a zinc ionophore and a pharmaceutically acceptable carrier.

10. The method of claim 9, wherein the zinc ionophore comprises zinc pyrithione, heterocyclic amines, dithiocarbamates and Vitamins.

11. The method of claim 10, wherein the zinc ionophore is zinc pyrithione.

12. The method of claim 10, wherein said heterocyclic amine is selected from the group consisting of 5,7-Diiodo-8-hydroxyquinoline and 8-Hydroxyquinoline.

13. The method of claim 10, wherein said dithiocarbamate is selected from the group consisting of pyrrolidine dithiocarbamate, zinc-diethyldithiocarbamate, disulfiram and zinc-dimethyldithiocarbamate.

14. The method of claim 10, wherein said vitamin is selected from the group consisting of Vitamin E and Vitamin A.

15. The method of claim 9, wherein the effective amount of a zinc ionophore ranges from about 0.005 µg per kg of body weight to about 5.0 mg per kg of body weight.

16. The method of claim 15, wherein the effective amount of a zinc ionophore ranges from about 0.2 µg per kg of body weight to about 600 µg per kg of body weight.

17. An anti-epileptic composition comprising a zinc ionophore and a pharmaceutically acceptable carrier.

18. A method of preventing seizures comprising administering to a subject in need thereof an effective amount of a zinc ionophore and a pharmaceutically acceptable carrier.

19. The method of claim 18, wherein the zinc ionophore comprises zinc pyrithione, heterocyclic amines, dithiocarbamates and Vitamins.

20. The method of claim 19, wherein the zinc ionophore is zinc pyrithione.

21. The method of claim 19, wherein said heterocyclic amine comprises 5,7-Diiodo-8-hydroxyquinoline and 8-Hydroxyquinoline.

22. The method of claim 19, wherein said dithiocarbamate comprises pyrrolidine dithiocarbamate, zinc-diethyldithiocarbamate, disulfiram and zinc-dimethyldithiocarbamate.

23. The method of claim 19, wherein said vitamin is selected from the group consisting of Vitamin E and Vitamin A.

24. The method of claim 18, wherein the effective amount of a zinc ionophore ranges from about 0.005 µg per kg of body weight to about 5.0 mg per kg of body body weight.

25. The method of claim 24, wherein the effective amount of a zinc ionophore ranges from about 0.2 µg per kg of body weight to about 600 µg per kg of body weight.

26. The method of claim 18, wherein the zinc ionophore is administered intravenously, intramuscularly, subcutaneously, intracerebroventricularly, orally or topically.

* * * * *